(12) United States Patent
Johnson et al.

(10) Patent No.: US 11,896,294 B2
(45) Date of Patent: Feb. 13, 2024

(54) METHOD AND SYSTEMS FOR REDUCING TREATMENT VARIABILITY AND INCREASING TREATMENT EFFICACY AND DURABILITY

(71) Applicant: Nuvaira, Inc., Plymouth, MN (US)

(72) Inventors: Philip J. Johnson, Plymouth, MN (US); Ryan Kaveckis, Minneapolis, MN (US); Martin L. Mayse, Wayzata, MN (US)

(73) Assignee: Nuvaira, Inc., Plymouth, MN (US)

( * ) Notice: Subject to any disclaimer, the term of this patent is extended or adjusted under 35 U.S.C. 154(b) by 747 days.

(21) Appl. No.: 16/467,426

(22) PCT Filed: Dec. 7, 2017

(86) PCT No.: PCT/US2017/065149
§ 371 (c)(1),
(2) Date: Jun. 6, 2019

(87) PCT Pub. No.: WO2018/106939
PCT Pub. Date: Jun. 14, 2018

(65) Prior Publication Data
US 2020/0222114 A1    Jul. 16, 2020

Related U.S. Application Data

(60) Provisional application No. 62/431,283, filed on Dec. 7, 2016.

(51) Int. Cl.
*A61B 18/14*    (2006.01)
*A61B 18/00*    (2006.01)

(52) U.S. Cl.
CPC .......... *A61B 18/1492* (2013.01); *A61B 2018/0072* (2013.01); *A61B 2018/00541* (2013.01);
(Continued)

(58) Field of Classification Search
CPC ...... A61B 18/1492; A61B 2018/00541; A61B 2018/00577; A61B 2018/00678;
(Continued)

(56) References Cited

U.S. PATENT DOCUMENTS 6,511,476 B2 * 1/2003 Hareyama .......... A61B 18/1206
606/41
7,608,275 B2   10/2009 Deem et al.
(Continued)

FOREIGN PATENT DOCUMENTS

EP         2662049 A2 * 11/2013 .......... A61B 5/6885
WO    WO 2014/143898 A1    9/2014
(Continued)

OTHER PUBLICATIONS

PCT International Search Report for PCT/US2017/065149, dated Feb. 13, 2018, 2 pages.
(Continued)

*Primary Examiner* — Linda C Dvorak
*Assistant Examiner* — Lindsay Regan Lancaster
(74) *Attorney, Agent, or Firm* — Husch Blackwell, LLP

(57) ABSTRACT

Methods and systems for ablating target tissue, such as in or along an airway, include modulation one of power and current of an a system to achieve a treatment output or parameter. Treatment outputs can include current, power, energy delivered, percent drop in impedance, an impedance-based ratio, a percent impedance slope, and/or an airway wall impedance. Power and/or current of the system can be varied, within certain maximum thresholds, such as power, current, and/or impedance thresholds, to achieve the desired output parameter target during some or all of the treatment time. The systems and methods reduce the variability of the treatment efficacy otherwise due to variability in electrical properties of patient tissue and/or electrode contact.

18 Claims, 15 Drawing Sheets

(52) U.S. Cl.
CPC ........... *A61B 2018/00577* (2013.01); *A61B 2018/00678* (2013.01); *A61B 2018/00702* (2013.01); *A61B 2018/00755* (2013.01); *A61B 2018/00821* (2013.01); *A61B 2018/00886* (2013.01); *A61B 2018/00898* (2013.01)

(58) Field of Classification Search
CPC ......... A61B 2018/00702; A61B 2018/0072; A61B 2018/00755; A61B 2018/00821; A61B 2018/00886; A61B 2018/00898; A61B 18/1815; A61B 2018/00023; A61B 2018/0022; A61B 2018/00642; A61B 2018/00791; A61B 2018/00875
See application file for complete search history.

(56) References Cited

U.S. PATENT DOCUMENTS

| | | | |
|---|---|---|---|
| 8,012,150 B2 * | 9/2011 | Wham | A61B 18/1206 606/38 |
| 8,088,127 B2 | 1/2012 | Mayse et al. | |
| 8,133,497 B2 | 3/2012 | Deem et al. | |
| 8,172,827 B2 | 5/2012 | Deem et al. | |
| 8,226,638 B2 | 7/2012 | Mayse et al. | |
| 8,338,164 B2 | 12/2012 | Deem et al. | |
| 8,483,831 B1 | 7/2013 | Hlavka et al. | |
| 8,489,192 B1 | 7/2013 | Hlavka et al. | |
| 8,660,647 B2 | 2/2014 | Parnis et al. | |
| 8,731,672 B2 | 5/2014 | Hlavka et al. | |
| 8,740,895 B2 | 6/2014 | Mayse et al. | |
| 8,777,943 B2 | 7/2014 | Mayse et al. | |
| 8,808,280 B2 | 8/2014 | Mayse et al. | |
| 8,821,489 B2 | 9/2014 | Mayse et al. | |
| 8,911,439 B2 | 12/2014 | Mayse et al. | |
| 8,932,289 B2 | 1/2015 | Mayse et al. | |
| 8,961,391 B2 | 2/2015 | Deem et al. | |
| 8,961,507 B2 | 2/2015 | Mayse et al. | |
| 8,961,508 B2 | 2/2015 | Mayse et al. | |
| 9,005,195 B2 | 4/2015 | Mayse et al. | |
| 9,017,324 B2 | 4/2015 | Mayse et al. | |
| 9,108,052 B2 | 8/2015 | Jarrard | |
| 9,125,643 B2 | 9/2015 | Hlavka et al. | |
| 9,149,328 B2 | 10/2015 | Dimmer et al. | |
| 9,339,618 B2 | 5/2016 | Deem et al. | |
| 9,398,933 B2 | 7/2016 | Mayse | |
| 9,498,283 B2 | 11/2016 | Deem et al. | |
| 9,539,048 B2 | 1/2017 | Hlavka et al. | |
| 9,649,153 B2 | 5/2017 | Mayse et al. | |
| 9,649,154 B2 | 5/2017 | Mayse et al. | |
| 9,662,171 B2 | 5/2017 | Dimmer et al. | |
| 9,668,809 B2 | 6/2017 | Mayse et al. | |
| 9,675,412 B2 | 6/2017 | Mayse et al. | |
| 9,867,986 B2 | 1/2018 | Hlavka et al. | |
| 9,931,162 B2 | 4/2018 | Mayse et al. | |
| 10,022,529 B2 | 7/2018 | Deem et al. | |
| 10,149,714 B2 | 12/2018 | Mayse et al. | |
| 10,201,386 B2 | 2/2019 | Mayse et al. | |
| 10,206,735 B2 | 2/2019 | Kaveckis et al. | |
| 10,252,057 B2 | 4/2019 | Hlavka et al. | |
| 10,363,091 B2 | 7/2019 | Dimmer et al. | |
| 10,368,937 B2 | 8/2019 | Kaveckis et al. | |
| 10,575,893 B2 | 3/2020 | Mayse | |
| 10,610,283 B2 | 4/2020 | Mayse et al. | |
| 10,729,897 B2 | 8/2020 | Deem et al. | |
| 2002/0151884 A1 * | 10/2002 | Hoey | A61B 18/14 606/41 |
| 2003/0171745 A1 * | 9/2003 | Francischelli | A61B 18/1442 606/41 |
| 2004/0010289 A1 | 1/2004 | Biggs et al. | |
| 2004/0226556 A1 | 11/2004 | Deem et al. | |
| 2005/0203504 A1 * | 9/2005 | Wham | A61B 18/1206 606/34 |
| 2006/0225742 A1 | 10/2006 | Deem et al. | |
| 2006/0235286 A1 | 10/2006 | Stone et al. | |
| 2008/0015563 A1 | 1/2008 | Hoey et al. | |
| 2011/0028963 A1 * | 2/2011 | Gilbert | A61B 18/1206 606/33 |
| 2011/0152855 A1 | 6/2011 | Mayse et al. | |
| 2011/0178569 A1 | 7/2011 | Parnis et al. | |
| 2011/0257647 A1 | 10/2011 | Mayse et al. | |
| 2011/0301587 A1 | 12/2011 | Deem et al. | |
| 2012/0221087 A1 | 8/2012 | Parnis et al. | |
| 2012/0302909 A1 | 11/2012 | Mayse et al. | |
| 2012/0310233 A1 | 12/2012 | Dimmer et al. | |
| 2012/0316552 A1 | 12/2012 | Mayse et al. | |
| 2013/0289556 A1 | 10/2013 | Mayse et al. | |
| 2013/0310822 A1 | 11/2013 | Mayse et al. | |
| 2014/0186341 A1 | 7/2014 | Mayse | |
| 2014/0257271 A1 | 9/2014 | Mayse et al. | |
| 2014/0276792 A1 | 9/2014 | Kaveckis et al. | |
| 2014/0371809 A1 | 12/2014 | Parnis et al. | |
| 2015/0112321 A1 * | 4/2015 | Cadouri | A61B 18/1206 606/34 |
| 2015/0148738 A1 * | 5/2015 | Caplan | A61M 25/1002 604/26 |
| 2016/0038725 A1 | 2/2016 | Mayse et al. | |
| 2016/0220851 A1 | 8/2016 | Mayse et al. | |
| 2016/0310203 A1 * | 10/2016 | Gaspredes | A61B 18/1445 |
| 2016/0310210 A1 | 10/2016 | Harshman et al. | |
| 2017/0014571 A1 | 1/2017 | Deem et al. | |
| 2017/0050008 A1 | 2/2017 | Mayse | |
| 2018/0028748 A1 | 2/2018 | Deem et al. | |
| 2018/0140346 A1 * | 5/2018 | Legaspi | A61B 5/053 |
| 2018/0199993 A1 | 7/2018 | Mayse et al. | |
| 2019/0105102 A1 | 4/2019 | Mayse et al. | |
| 2019/0142510 A1 | 5/2019 | Mayse et al. | |
| 2019/0142511 A1 | 5/2019 | Wahr et al. | |
| 2019/0151018 A1 | 5/2019 | Mayse et al. | |
| 2020/0001081 A1 | 1/2020 | Hlvaka et al. | |
| 2020/0060750 A1 | 2/2020 | Kaveckis et al. | |
| 2020/0085495 A1 | 3/2020 | Dimmer et al. | |
| 2020/0222114 A1 | 7/2020 | Johnson et al. | |
| 2020/0268436 A1 | 8/2020 | Mayse | |

FOREIGN PATENT DOCUMENTS

| | | |
|---|---|---|
| WO | WO 2014/160422 A1 | 10/2014 |
| WO | WO 2015/038886 A1 | 3/2015 |
| WO | WO 2015/089377 A1 | 6/2015 |

OTHER PUBLICATIONS

PCT Written Opinion of the ISA for PCT/US2017/065149, dated Feb. 13, 2018, 10 pages.

Communication dated Jun. 22, 2020 for EP Application No. 17877676.1, 7 pages.

* cited by examiner

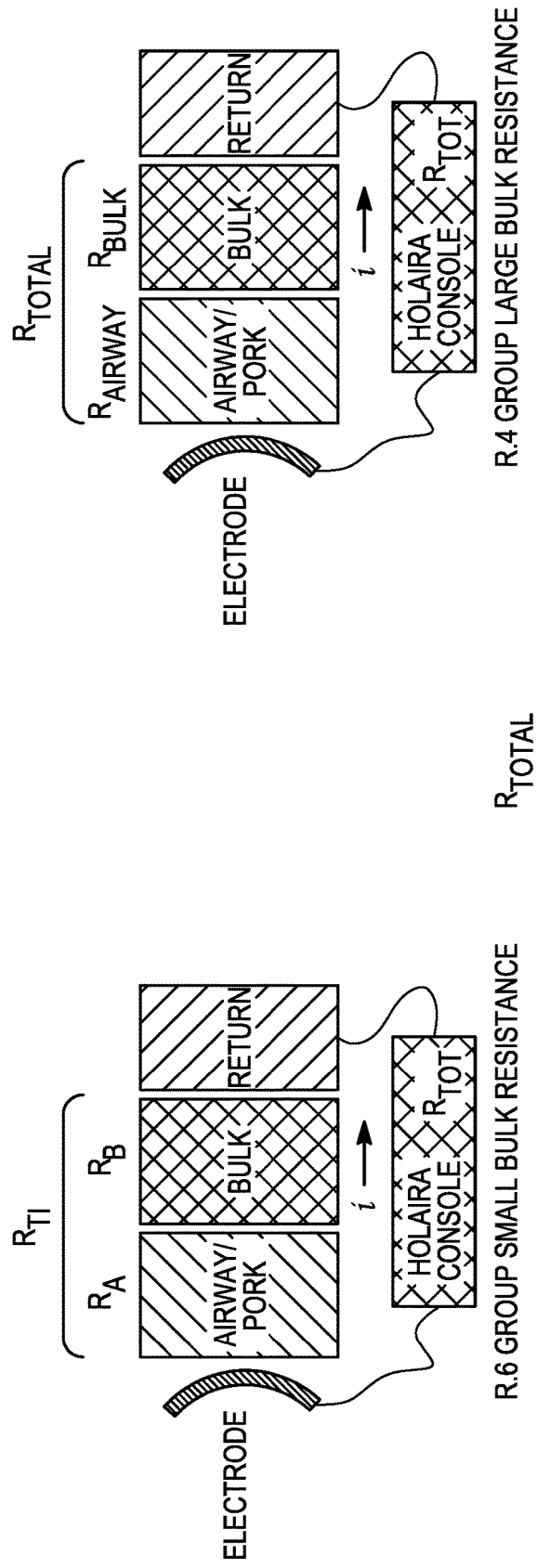

METHOD AND SYSTEMS FOR REDUCING TREATMENT VARIABILITY AND INCREASING TREATMENT EFFICACY AND DURABILITY

RELATED APPLICATION

The present application is a National Phase entry of PCT Application No. PCT/US2017/065149, filed Dec. 7, 2017, which claims the benefit of U.S. Provisional Application No. 62/431,283, filed Dec. 7, 2016, which is hereby incorporated herein in its entirety by reference.

TECHNICAL FIELD

The invention relates generally to treatment systems and methods, and more particularly, to pulmonary treatment systems and methods for controlling energy delivery to an airway while compensating for variability in the electrical properties of patient tissue.

BACKGROUND

Pulmonary diseases are some of the most common medical conditions, affecting tens of millions of people in the U.S. alone. Pulmonary diseases result from problems in the respiratory tract that interfere with proper respiration. Many of these diseases require medical attention or intervention in order to restore proper lung function and improve a patient's overall quality of life. Some of the more common pulmonary diseases include asthma and chronic obstructive pulmonary disease or COPD. Symptoms of pulmonary disease like COPD and asthma vary but often include a persistent cough, shortness of breath, wheezing, chest tightness, and breathlessness. Generally, these symptoms are exacerbated when performing somewhat strenuous activities, such as running, jogging, brisk walking, etc. However, these symptoms may be noticed when performing non-strenuous activities, if the disease is allowed to progress unchecked. Over time, especially if medical attention is not sought, a person's daily activities will be significantly impaired, thus reducing overall quality of life.

Many pulmonary diseases, whether acute or chronic, often involve pathologic conditions associated with airway inflammation. When such inflammation has developed at the airway, infiltrated inflammatory cells cause damage to bronchial or lung tissue, which eventually results in the respiratory dysfunction characteristic of pulmonary diseases, such as reduction in respiratory flow rate or oxygen exchange capacity. Over time, this inflammation can lead to blockage of the airway lumen, thickening of the airway wall, and alteration of structures within or around the airway wall. Airway obstruction can significantly decrease the amount of gas exchanged in the lungs resulting in breathlessness. Blockage of an airway lumen can be caused by excessive intraluminal mucus, edema fluid, or both. Thickening of the airway wall may be attributable to excessive contraction of the airway smooth muscle, airway smooth muscle hypertrophy, mucous glands hypertrophy, inflammation, edema, or combinations of these. Alteration of structures around the airway, such as destruction of the lung tissue itself, can lead to a loss of circumferential traction on the airway wall and subsequent narrowing of the airway. Generally, pulmonary diseases like COPD and asthma are the result of a complex interplay of local inflammatory cytokines, inhaled irritants (e.g., cold air, smoke, allergens, or other chemicals), systemic hormones (e.g., cortisol and epinephrine), local nervous system input (i.e., nerve cells contained completely within the airway wall that can produce local reflex stimulation of smooth muscle cells and mucous glands), and the central nervous system input (i.e., nervous system signals from the brain to smooth muscle cells and mucous glands carried through the vagus nerve).

Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and coughing. Additionally, COPD, often referred to as emphysema, is characterized by the alteration of lung tissue surrounding or adjacent to the airways in the lungs. Emphysema can involve destruction of lung tissue (e.g., alveolar sacs) that leads to reduced gas exchange and reduced circumferential traction applied to the airway wall by the surrounding lung tissue. The destruction of alveoli tissue restricts the in-flow of oxygen rich air and the proper function of healthier tissue, resulting in significant breathlessness. Exposure to chemicals or other substances (e.g., tobacco smoke) may significantly accelerate the rate of tissue damage or destruction. Additionally, chronic bronchitis, another type of COPD, is characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent.

Treatment for pulmonary diseases includes reducing exposure to harmful agents, administering medications (e.g., bronchodilators, steroids, phosphodiesterase inhibitors, theophylline, antibiotics, etc.), administering lung therapy (e.g., oxygen therapy, pulmonary rehabilitation), and surgical intervention, such as bronchial thermoplasty. Unfortunately, pharmacological treatment requires patient compliance, often causes harmful side effects, and does not necessarily treat the underlying cause of the disease. Similarly, surgical intervention can result in the destruction of smooth muscle tone and nerve function, such that the patient is unable to respond favorably to inhaled irritants, systemic hormones, and both local and central nervous system input.

An alternative method for treating pulmonary disease is referred to as targeted lung denervation. This method utilizes ablation, such as monopolar or biopolar radiofrequency (RF) ablation, via an ablation assembly to selectively treat target regions inside of the airway wall (e.g., anatomical features in the stromas) while protecting the superficial tissues, such as the surface of the airway wall. For example, the mucous glands can be damaged to reduce mucus production a sufficient amount to prevent the accumulation of mucus that causes increased air flow resistance while preserving enough mucus production to maintain effective mucociliary transport, if needed or desired. Nerve branches/fibers passing through the airway wall or other anatomical features in the airway wall can also be destroyed.

Specially designed catheters allow for the introduction of an ablation assembly, generally comprising one or more collapsible electrodes or energy emitters, coupled to an expandable member, such as a balloon, into the airway of a patient via a delivery device. The delivery device can be a guide tube, a delivery sheath, a bronchoscope, or an endoscope and can include one or more viewing devices, such as optical viewing devices (e.g., cameras), optical trains (e.g., a set of lens), optical fibers, CCD chips, and the like. Once positioned in the desired region of the airway, such as the left and/or right main bronchi, the expandable member is expanded to position the one or more electrodes in contact with the airway wall.

Energy, such as RF energy, is supplied to the energy emitter to ablate the targeted tissue, causing a lesion to form, therefore temporarily or permanently damaging the targeted tissue, therefore affecting, e.g. attenuating nerve signals to or from, portions of the lungs associated with the targeted tissue. Simultaneously, a coolant is supplied through the catheter and is directed to the one or more electrodes and into the expandable member or balloon. This allows for cooling of the superficial tissue in contact with the electrode, as well as the adjacent tissues. The size, shape, and depth of the lesions are determined by the flow rate and temperature of the coolant, and the energy supplied to the energy emitter(s). Devices, systems, and methods of such procedures can be found, for example, in one or more of U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which are incorporated herein by reference in their entireties.

In order to ensure that most or all of the target nerves extending along the airway are treated, it is generally desirable to form a circumferential lesion around all or most of the circumference of the airway wall. Due to design constraints or preferences, the electrode or energy emitter may not extend around the entirety of the circumference of the airway wall. Therefore, a circumferential lesion may be formed by ablating tissue while slowly rotating the ablation assembly or by positioning the ablation assembly in a series of rotational positions at each of which energy is delivered for a desired time period. The adjacent lesions then become contiguous and form a circumferential band all the way around the airway wall. Additionally or alternatively, the catheter may be repositioned axially to treat other locations within the airway distally or proximally of the first treatment site.

With respect to monopolar RF ablation systems, the systems generally include two separate monopolar electrodes, the active electrode (i.e., the energy emitter of the ablation assembly) and the dispersive electrode (e.g., a pad), which in combination with the patient's body, completes a circuit. The active electrode is designed to focus the current or power on the therapeutic target thereby creating a desired tissue effect, such as ablation. The dispersive electrode is positioned on the patent in a location remote from the surgical site and is relatively large in surface area, a design that serves to defocus or disperse the current thereby preventing or reducing the occurrence of non-target tissue injury. However, the variability of the electrical properties of the patient tissue interposed between the two electrodes of a monopolar system affects the consistency of the therapeutic effect.

The variability of intended effect under constant ablation parameters (i.e., constant power, current, and/or time) is well recognized in the field of monopolar RF ablation. Multiple methods can be found in the literature that have been employed to counter this inherent variability. These methods include monitoring electrode/tissue interface temperature, tissue temperature, impedance change during energy delivery, and force applied to the electrode/tissue interface to maintain contact.

To better address the challenges of variability in monopolar RF ablation and to compensate for variability in the treatment, including variability in patient tissue and/or electrode/tissue contact, there remains a need for an improved system, method, and algorithm for the treatment of tissue.

SUMMARY

Embodiments of the invention are directed to a pulmonary treatment system including a catheter assembly including a targeted lung denervation (TLD) device, such as an RF, microwave, or ultrasound catheter, and generally includes an elongate shaft having proximal and distal portions, and an ablation assembly coupled to the distal portion of the shaft, the ablation assembly including an expandable member, such as a balloon or basket, and one or more electrodes or energy emitters coupled to the expandable member.

The catheter assembly is further fluidly and electrically coupled to a system console, including a coolant supply and return reservoir, and an energy supply such as a RF generator, via the handle assembly. The system further includes one or more sensors and a controller for measuring treatment properties or outputs, such as, for example, tissue and energy properties including, but not limited to, tissue impedance, tissue temperature, output current and/or voltage, etc.), and for adjusting treatment parameters based on one or more of the treatment outputs. The controller can generally include a microprocessor operably connected to a volatile type memory (e.g., RAM) and/or a non-volatile type memory (e.g., flash media, disk media, etc.) for collecting and storing, either continuously or discretely, output data from the sensors. The microprocessor is also operably connected to the energy emitter(s) and generator, and is programmed to process and calculate output data from the sensors, and/or control the output of the generator and/or energy emitter(s) according to either open and/or closed control loop schemes, as described below.

Methods and systems of embodiments of the invention include varying one of power and current of the system to achieve a treatment output or parameter. In a first embodiment, generator power is varied, within a maximum power threshold, to achieve a constant current during the treatment time. In another embodiment, tissue impedance is measured and a percent drop in impedance is calculated during the duration of treatment. The current is varied, within a maximum power threshold, to achieve a desired percent drop in impedance during the treatment time.

In yet another embodiment, generator power is varied, within a maximum power threshold, to achieve a constant current at a desired current target during the treatment time. Also during the entirety of the treatment time, the percent drop in impedance is calculated. If a predetermined percent drop in impedance is reached before the desired current target is reached, the current is held constant at that time for the remainder of the treatment time. If the predetermined percent drop in impedance is not reached during the treatment time, the current is maintained at the desired current target for the remainder of the treatment time.

In another embodiment of the invention, during a first portion of the treatment time, the power is varied to achieve a desired current target. Upon expiration of the first portion of the treatment time, the power is held constant for the remainder of treatment time. If, however, the impedance during the second portion of the treatment time meets or exceeds a sum of a lower impedance value sampled during the first portion of the treatment time and a predetermined impedance value, the system delivers a warning or ceases energy delivery altogether.

In another embodiment, during a first portion of the treatment time, the power or the current is held constant at a desired value. Upon expiration of the first portion of the treatment time, the power or current is varied, within a maximum power limit to maintain a small, positive percent impedance slope, such as between 1%-30%. The impedance slope is calculated by impedance measurements over the course of treatment. In this embodiment, if an impedance limit threshold is met or exceeded during the first portion of the treatment time, the system delivers a warning or ceases energy delivery altogether. For the second portion of the treatment time, if either a impedance limit threshold or a percent impedance slope limit threshold is exceeded, the system delivers a warning or ceases energy delivery altogether.

In another embodiment, over the course of the entire treatment the impedance of the airway wall is determined or closely approximated to allow for continuous modulation of current to maintain a constant power being deposited within airway wall. The airway wall impedance could be determined or approximated using a split primary electrode that acts jointly as a bipolar impedance detecting element and a monopolar active electrode that concentrates therapeutic current. The airway wall impedance could be approximated by using another electrode placed in location in close anatomical proximity to the active electrode in the airway such as the esophagus or adjacent blood vessels. By measuring the impedance between the two electrodes, an approximation of the airway wall component of the total resistance could be determined.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 6A-6C are test group monopolar RF ablation circuits according to an embodiment of the invention;

Figure 1:
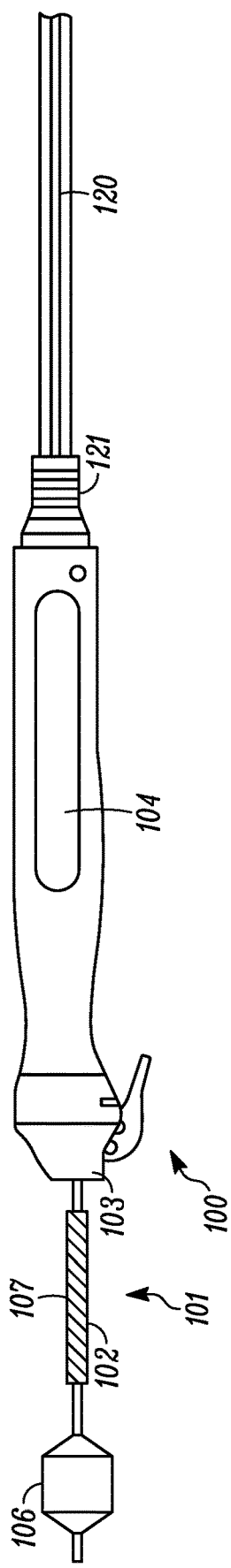
FIG. 1 is a treatment system according to an embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Throughout this disclosure, the words disrupt, ablate, modulate, denervate will be used. It should be understood that these globally refer to any manipulation of the nerve that changes the action of that nerve. This can be a total cessation of signals, as in ablation or severing, or it can be a modulation, as is done by partial or temporary disruption, pacing, etc.

Similarly, trachea is often used to describe a segment wherein the devices and methods will be used. It should be understood that this is shorthand and can be meant to encompass the trachea itself, as well as the right and left main bronchi and other portions of the pulmonary tree as necessary.

It should be noted that the pulmonary nerves referred to in the disclosure not only include nerves that innervate the pulmonary system but also any neural structures that can influence pulmonary behavior. For example, elements of the cardiac plexus, or the nerves that innervate the esophagus, also interact with the airways and may contribute to asthmatic conditions. The nerves can include nerve trunks along the outer walls of hollow vessels, nerve fibers within the walls of hollow vessels (e.g., the wall of the trachea and/or esophagus), nerves within a bridge between the trachea and esophagus, or at other locations. The left and right vagus nerves originate in the brainstem, pass through the neck, and descend through the chest on either side of the trachea. These or a portion of these nerves can be targeted. The vagus nerves spread out into nerve trunks that include the anterior and posterior pulmonary plexuses that wrap around the trachea, the left main bronchus, and the right main bronchus. The nerve trunks also extend along and outside of the branching airways of the bronchial tree. Nerve trunks are the main stem of a nerve comprising a bundle of nerve fibers bound together by a tough sheath of connective tissue. The vagus nerves, including their nerve trunks, along the trachea or other nerve tissue along, proximate to, or in the bronchial tree can be targeted, while branches that run along, proximate to, or in the esophagus can be not targeted and/or protected via the embodiments set forth below. A treatment device in the form of a tracheal device can be positioned at different locations within an airway (e.g., the trachea, one of the main stem bronchi, or other structures of the bronchial tree).

The pulmonary branches of the vagus nerve along the left and right main stem bronchus intermedius are particularly preferred targets. The nerve trunks of the pulmonary branches extend along and outside of the left and right main stem bronchus and distal airways of the bronchial tree. Nerve trunks of the main stem nerve comprise a bundle of nerve fibers bound together by a tough sheath of connective tissue. Any number of procedures can be performed on one or more nerve trunks to affect the portion of the lung associated with those nerve trunks. Because some of the nerve tissue in the network of nerve trunks coalesce into other nerves (e.g., nerves connected to the esophagus, nerves though the chest and into the abdomen, and the like), specific sites can be targeted to minimize, limit, or substantially eliminate unwanted damage of those other nerves.

Some fibers of anterior and posterior pulmonary plexuses coalesce into small nerve trunks which extend along the outer surfaces of the trachea and the branching bronchi and bronchioles as they travel outward into the lungs. Along the branching bronchi, these small nerve trunks continually ramify with each other and send fibers into the walls of the airways. Any of those nerve trunks or nerve tissue in walls can be targeted.

The aspects, embodiments, features, systems, devices, materials, methods and techniques described herein may, in some embodiments, be similar to any one or more of the embodiments, features, systems, devices, materials, methods and techniques described in any one or more of the following applications and patents: PCT Publication Nos. WO2014/143898 and WO2015/038886, both to Mayse et al.; U.S. Patent Application Publication Nos. 2011/0152855 to Mayse et al., 2011/0301587 to Deem et al., 2012/0310233 to Dimmer et al., 2013/0310822 to Mayse et al., 2014/0186341 to Mayse, and 2014/0257271 to Mayse et al.; U.S. Pat. No. 8,088,127 to Mayse et al., U.S. Pat. No. 8,172,827 to Deem et al., U.S. Pat. No. 8,483,831 Hlavka et al., and U.S. Pat. No. 8,911,439 to Mayse et al. Further, the systems and methods disclosed herein can employ any of the cooling systems described in U.S. Patent Application Publication No. 2014/0276792 and PCT Publication No. WO2014/160422, both to Kaveckis et al., and/or any of the handle systems described in PCT Publication Nos. WO2015/089377 to Harshman et al. The disclosures of each of the above-identified applications and patents are hereby incorporated by reference in their entireties, except for the claims and any expressly contradictory definitions.

According to certain embodiments of the invention, devices may be configured for the delivery of radio frequency energy to modulate or disable the pulmonary plexus. While embodiments shown are configured for delivery of RF energy, many of the configurations can also be adapted to accommodate a catheter based microwave antenna, high energy pulse electroporation, or similar energy modalities.

The RF energy can be delivered in a traditional conductive mode RF, where the energy is directly applied to the tissue through a direct contact electrode, or it can be delivered through the use of capacitive coupling to the tissue. In capacitive coupling, a slightly higher frequency signal is typically used compared to traditional RF, and the energy is delivered to the tissue across a dielectric, which is often a cooling element. In one example of capacitive coupling, energy may be delivered across a cooling plate that keeps the surface of tissue contacted from being harmed as energy is delivered deeper into the target tissue.

The RF energy can be delivered to different target regions, which can include, without limitation, nerve tissue (e.g., tissue of the vagus nerves, nerve trunks, etc.), fibrous tissue, diseased or abnormal tissues (e.g., cancerous tissue, inflamed tissue, and the like), cardiac tissue, muscle tissue, blood, blood vessels, anatomical features (e.g., membranes, glands, cilia, and the like), or other sites of interest.

In RF ablation, heat is generated due to the tissue resistance as RF electrical current travels through the tissue. The tissue resistance results in power dissipation that is equal to the current flow squared times the tissue resistance. To ablate deep tissues, tissue between an RF electrode and the deep tissue can become overheated if active cooling is not employed using a cooling device, such as a cooling plate or cooling balloon. The cooling device can be used to keep tissue near the electrode below a temperature that results in cell death or damage, thereby protecting tissue. For example, cooling can prevent or limit overheating at the electrode-tissue interface. Overheating (e.g., tissue at temperatures above 95° C. to about 110° C.) can lead to the formation of coagulum, tissue desiccation, tissue charring, and explosive outgassing of steam. These effects can result in increased tissue resistance and reduced RF energy transfer into the tissue, thereby limiting the effective RF ablation lesion depth. Active cooling can be used to produce significantly deeper tissue lesions. The temperature of coolant for active cooling can be about 0° C. to about 24° C. In some embodiments, the coolant and electrode produce a lesion at a therapeutic depth of at least about 3 mm while protecting tissue at shallower depths from lethal injury. In some embodiments, the lesions can be formed at a depth of about 3 mm to about 5 mm to damage nerve tissue. Other temperatures and depths can be achieved.

According to an exemplary embodiment, as illustrated in FIG. 1, an RF treatment system 100 can comprise an ablation catheter assembly 101 having an elongate shaft 102 and an ablation assembly 106 coupled to a first or distal end of shaft 102, a positioning handle assembly 104 coupled to a second or proximal end of shaft 102, an optional insertion tube 107 movably coupled to shaft 102 between ablation assembly 106 and handle assembly 104, and a scope coupling assembly 103 for coupling catheter assembly 101 and handle assembly 104 to a working channel of a delivery device, such as a flexible endoscope or bronchoscope.

Figure 2:
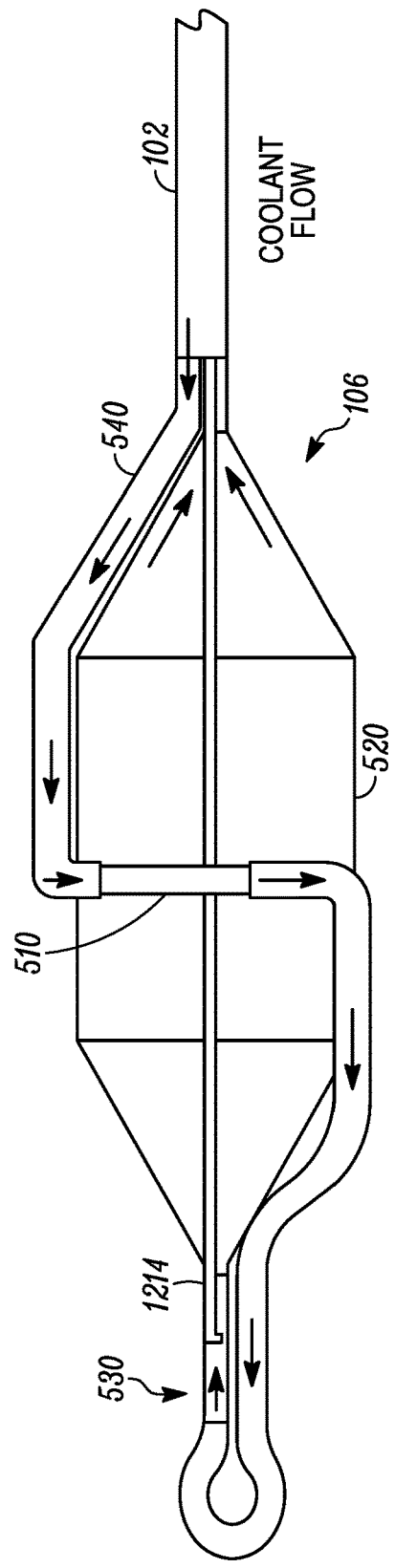
FIG. 2 is an ablation assembly according to an embodiment of the invention.

Referring to FIG. 2, ablation assembly 106 can comprise one or more energy emitters 510, such as an electrode or transducer, and an expandable member 520, such as a balloon or basket. One or more energy emitters are configured to delivery energy in the form of RF, microwave, or ultrasound, for example. In embodiments, one or more energy emitters is coupled to a conduit 540 configured for flowing coolant therethrough to cool energy emitters 510. Conduit 540 is in fluid communication with shaft 102 and expandable member 520 for circulating coolant. Ablation assembly 106 can comprise a coolant fluid path or cooling circuit to cool energy emitter 510 and a surface of expandable member 520 to protect surface tissue in contact with energy emitter 510 and adjacent to energy emitter 510 to accomplish deep tissue ablation.

Ablation assembly 106 can optionally comprise a throttle valve 530 for regulating the flow between conduit 540 and expandable member 520. Ablation assembly 106 can also optionally comprise a support wire 1214, such as a Nitinol wire to provide added axial, torsional, and buckling support for expandable member 520 and catheter shaft 102. Further details of ablation assemblies 106 are described in U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which were incorporated by reference in their entireties above.

In some embodiments, and referring to FIG. 1, handle assembly 104 is coupled to the proximal portion of shaft 102 of catheter assembly 101. An umbilical cable 120 coupled to an end of handle assembly 104 via strain relief 121 for fluidly and/or electrically coupling catheter assembly 101 to accompanying devices or accessories, such as a power source, energy source (e.g. RF generator), fluid or coolant supply, heat exchanger, and controller, preferably combined in a system console. Umbilical cable 120 can include, for example, connections for inlet and return fluid tubes or lumens for fluidly coupling shaft 102 to a fluid or coolant supply, from the console which optionally includes a heat exchanger for cooling and/or heating input fluid, and one or more electrical cable/connector to electrically connect the shaft and/or ablation assembly to a power source, thermocouples for temperature monitoring, and/or pressure sensors for coolant circuit pressures. Suitable handle assemblies are described in more detail in International Publication No. WO 2015/089377 A1, entitled "Catheter and Handle Assembly, Systems, and Methods", incorporated herein by reference in its entirety.

Catheter assembly 101 is further fluidly and electrically coupled to a system console (not shown), including a coolant circuit (at 600 shown in FIG. 3 described below) including coolant supply and return reservoir, and an energy supply such as a RF generator, via handle assembly 104. Handle assembly 104 is configured to maneuver the distal portion or end of shaft 102 and therefore ablation assembly 106 in axial and circumferential directions during the administration of treatment, such as targeted lung denervation (TLD) therapy, details of which are discussed in U.S. Pat. No. 8,088,127 and U.S. Patent Application Publication No. 2011/0152855, both of which were incorporated by reference in their entireties above.

Figure 3:
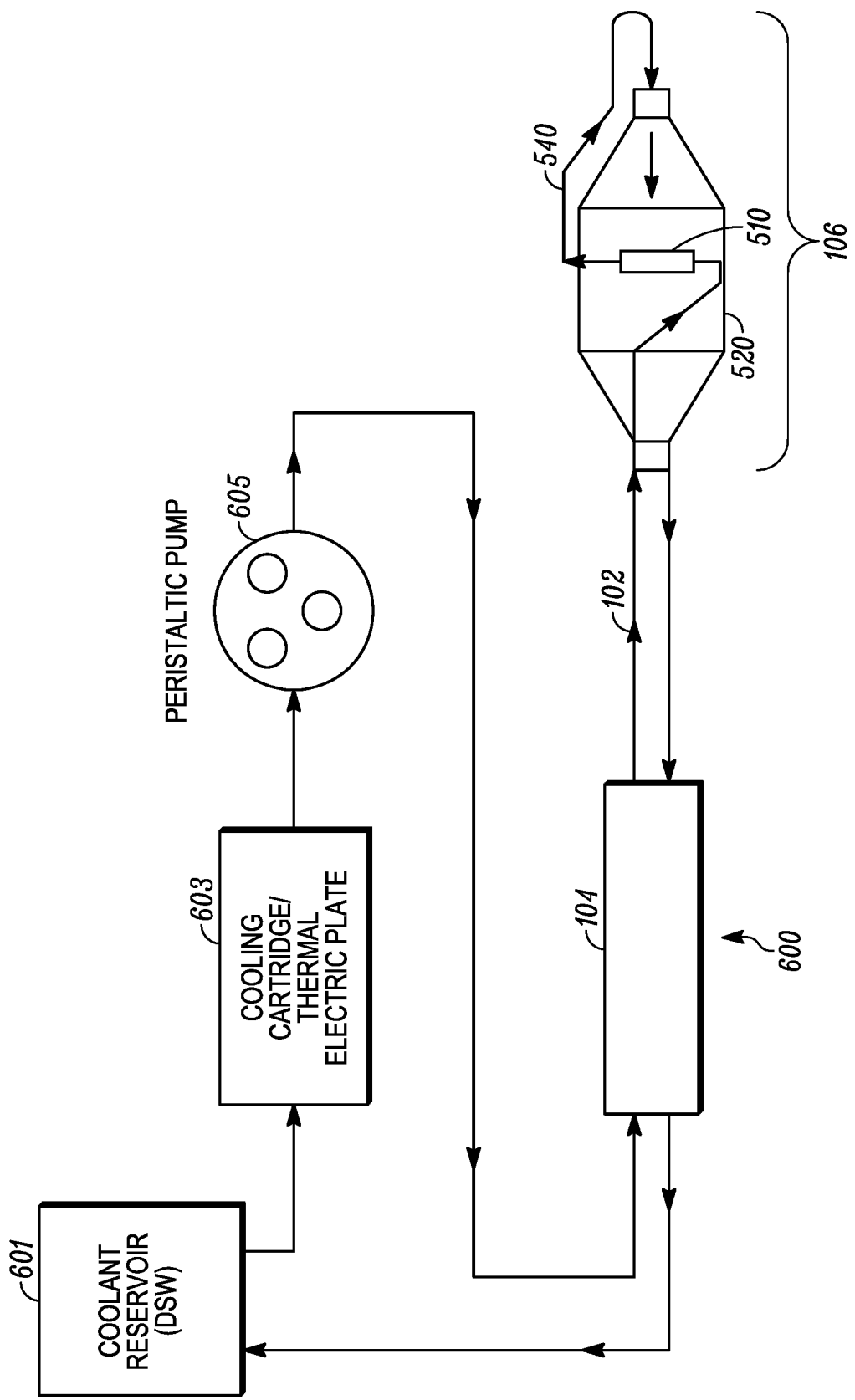
FIG. 3 is a cooling circuit for the treatment system of FIG. 1 according to an embodiment of the invention.

As depicted in FIG. 3, cooling circuit 600 includes coolant supplied from a reservoir 601 of a system console, through an optional heat exchanger 603 of the system console, through handle 104, through an inflow lumen in shaft 102, through conduit 540 to which electrode 510 is coupled, through expandable member 520, through an outflow lumen in shaft 102, through handle 104, and back to the system console. Non-limiting examples of a system console can be found in U.S. Patent Application Publication No. 2013/0289556, entitled "Delivery Devices with Coolable Energy Emitting Assemblies" and U.S. Pat. No. 8,489,192 entitled "System and Method for Bronchial Dilation," both of which are incorporated by reference in their entireties. Cycling of the fluid is accomplished, for example, by a peristaltic pump 605. In an alternative embodiment, the flow is reversed such that the coolant flows through the expandable member before the electrode.

Now referring back to FIG. 2, as discussed above, ablation assembly 106 includes one or more energy delivery elements in the form of RF electrode(s) 510. The electrode 510 can be brought into contact with or proximate to an inner surface of the trachea. The RF electrode 510 can output RF energy, converted from the DC or AC power supplied from the generator, which travels through the tissue and is converted into heat. The heat causes formation of a lesion. The RF energy can be directed radially outward towards the targeted tissue without causing appreciable damage to non-targeted tissue (e.g., tissue of or associated with the esophagus, inner tissue of the trachea, anterior tissue of the trachea, etc.) using coolant. A wide range of different procedures, such as, for example, denervation of a portion of the trachea, an entire circumference of the trachea, target nerve trunks travelling to one lung or both lungs, or the like. Nerve tissue is damaged to relax the muscle tissue in the bronchial tree to dilate the airway to reduce air flow resistance in one or both lungs, thereby allowing more air to reach the alveolar sacs for the gas exchange process. Decreases in airway resistance may indicate that passageways of airways are opening, for example in response to attenuation of nervous system input to those airways.

In embodiments, the ablation assembly 106 further includes sensors which are used to monitor temperatures, inflation pressures, coolant flow rates, tissue impedance, current, power, or other parameters of interest. Feedback from the sensors can be used to modulate the power and/or current delivered to electrode(s). Outputted energy can be adjusted to account for local variations in tissue that alters the local impedance, thus avoiding excess heating which can lead to unwanted hot spots. Lesions can also be formed independent of regional tissue characteristics.

In one embodiment, the ablation assembly has one or more sensors (not shown) positioned thereon and that are communicatively coupled to a controller in the console. The controller can command the catheter assembly 101 based on signals from the sensor (e.g., a pressure sensor, a temperature sensor, a thermocouple, current sensor, power sensor, impedance sensor, a contact sensor, or the like). Sensors can also be positioned along the elongate shaft 102 or at any other location.

The controller is configured for measuring treatment properties or outputs, such as, for example, tissue and energy properties including, but not limited to, tissue impedance, tissue temperature, output current and/or voltage, etc.), calculating certain mathematical outputs or relationships based on the sensor readings, and/or for adjusting treatment parameters based on one or more of the treatment outputs. The controller can generally include a microprocessor operably connected to a volatile type memory (e.g., RAM) and/or a non-volatile type memory (e.g., flash media, disk media, etc.) for collecting and storing, either continuously or discretely, output data from the sensors. The microprocessor is also operably connected to the energy emitter(s) and generator, and is programmed to process and calculate output data from the sensors, and/or control the output of the generator and/or energy emitter(s) according to either open and/or closed control loop schemes, as described below.

The controller can be a closed loop system or an open loop system. For example, in a closed loop system, the electrical energy is delivered to the electrode 510 based upon feedback signals from one or more sensors configured to transmit (or send) one or more signals indicative of one or more tissue characteristics, energy distribution, tissue temperatures, or any other measurable parameters of interest. Based on those readings, the controller adjusts operation of the electrode 510. Alternatively, in an open loop system, the operation of the electrode 510 is set by user input. For example, the user can observe tissue temperature or impedance readings and manually adjust the power and/or current level delivered to the electrode 510. Alternatively, the power can be set to a fixed power mode. In yet other embodiments, a user can repeatedly switch between a closed loop system and an open loop system.

Mathematics Behind Heat Generation in Target Tissue

Figure 4:
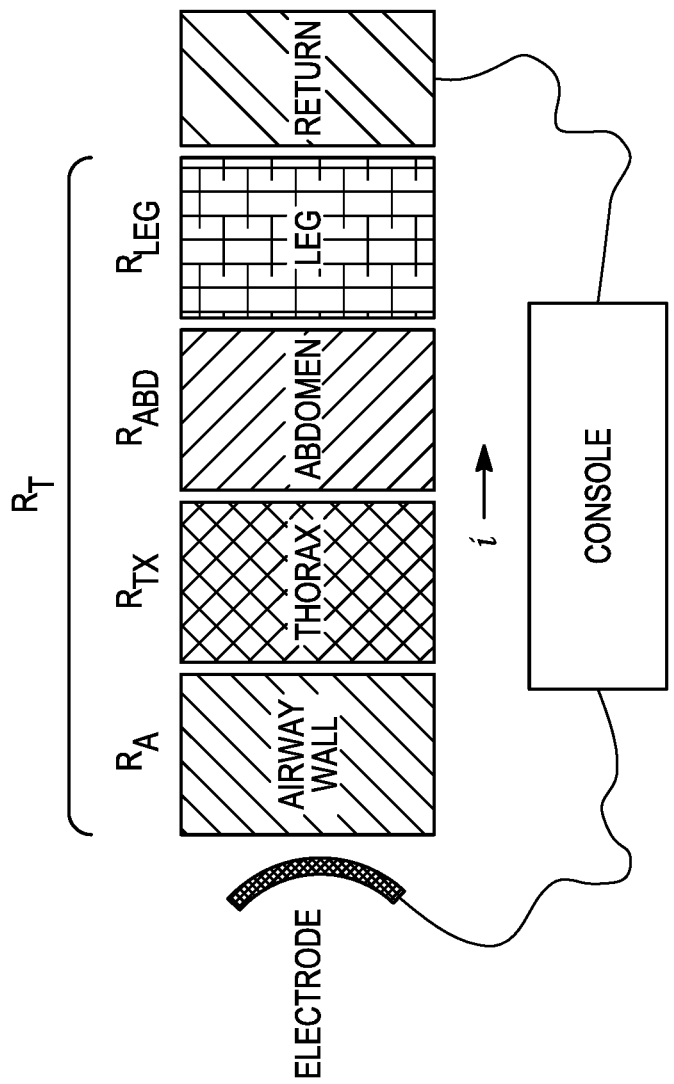
FIG. 4 is a depiction of a monopolar RF ablation circuit according to an embodiment of the invention.

Referring now to FIG. 4, and as discussed above, a monopolar RF ablation system 400 generally includes two separate electrodes, an active electrode 402, and a dispersive electrode 404, and a system console 406 for powering the active electrode 402. The electrodes 402, 404 include the active electrode 402 (i.e., an energy emitter of the ablation assembly as described above) and the dispersive electrode 404 (e.g., a pad), which in combination with the patients body, such as the airway A, thorax TX, abdomen Abd, and leg Leg, completes a circuit. All possible components of the patient's body that do not include the airway will be referred to as the bulk B. The active electrode 402 is designed to focus the current or power on the therapeutic target thereby creating a desired tissue effect, such as ablation. The dispersive electrode 404 is positioned on the patient in a location remote from the surgical site and is relatively large in surface area, a design that serves to defocus or disperse the current thereby preventing or reducing the occurrence of non-target tissue injury.

Figure 5:
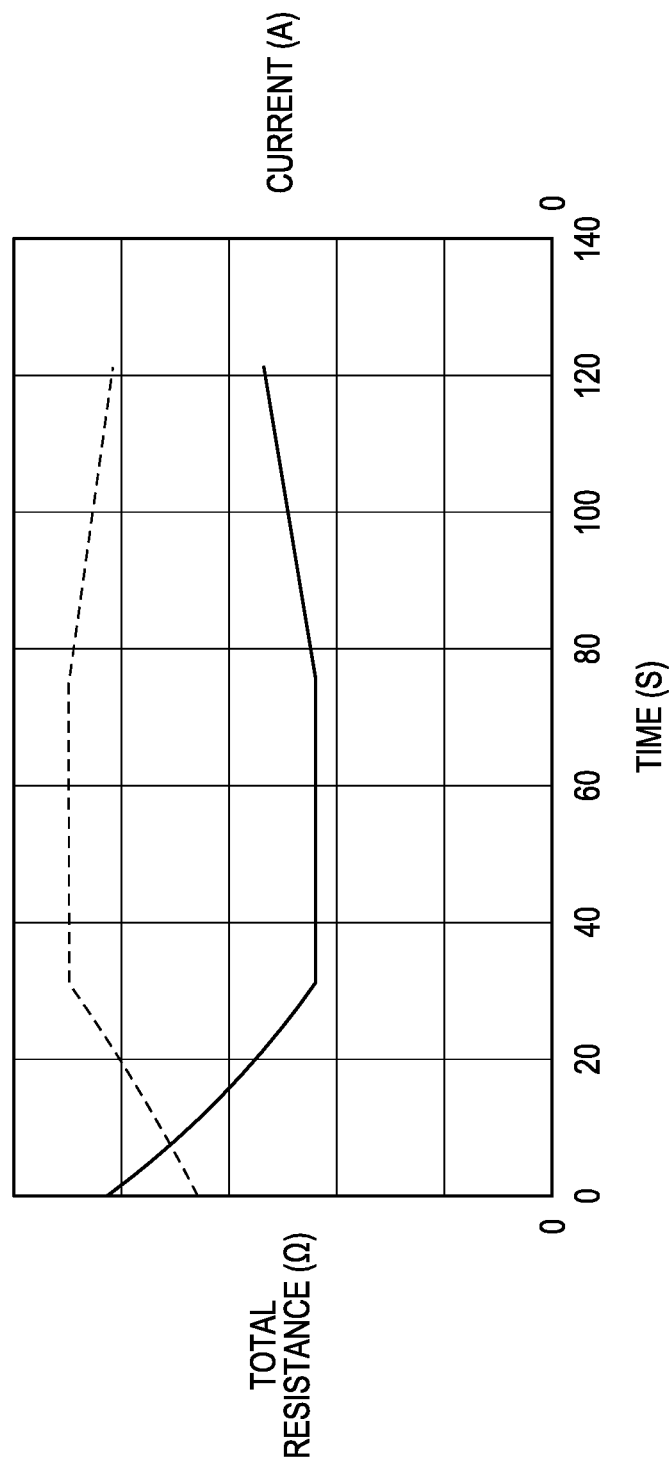
FIG. 5 is a graph of an inverse correlation of total resistance and current over time for the circuit of FIG. 4.

As discussed above, in RF ablation, heat is generated due to the tissue resistance as RF electrical current travels through the tissue. The tissue resistance results in power dissipation that is equal to the current flow squared times the tissue resistance:

$$P = i^2 R_T$$

where i is the current, and $R_T$ is the total resistance of the circuit, or the resistors in series, i.e., the airway wall, thorax, abdomen, and leg of the body. As suggested by the mathematical relationship, current varies inversely with total resistance, as shown in FIG. 5. Specifically, at constant power, as current increases, total resistance decreases, and heat is generated in the target tissue of the airway wall based on current and the airway resistance, $R_A$.

According to the First Law of Thermodynamics, change in energy in the airway system $\Delta E_A$ can be expressed as a change in temperature of the airway $\Delta T_A$, mass m and specific heat c as $$\Delta E_A = mc\Delta T_A,$$

which can be rewritten for a defined volume V and with a density p, as $$\Delta E_A = \rho Vc \Delta T_A.$$

Realizing that, in steady state, energy in the airway is the power being input to the airway, $P_A$, multiplied by the time, t, over which the power has been input into the airway, then $$\Delta E_A = tP_A,$$

and then solving for $\Delta T_A$ yields:

$$\Delta T_A = P_A t / \rho Vc$$

$$P_A = (R_A / (R_A + R_B)) \times P_T,$$

$$\Delta T_A = (P_T t / \rho Vc) \times (R_A / (R_A + R_B)).$$

Understanding this relationship, a test was conducted that demonstrated a power increase could compensate for an increase in bulk resistance $R_B$, to produce a similar temperature effect in the airway. The test also demonstrated that it is possible to monitor how an activation is progressing based on impedance changes, and through manual power changes the impedance drop can be changed. The test consisted of three test groups, shown in FIGS. 6A-6C, and included a small bulk resistance group ($R_A/R_T=0.6$) at constant power (20 W) for the treatment time (120 seconds), a large bulk resistance group ($R_A/R_T=0.4$) at constant power (20 W) for the treatment time (120 seconds), and a large bulk resistance group ($R_A/R_T=0.4$) which included constant power (20 W) for 30 seconds, and then an increase in power (+10 W) at 30 seconds for the remaining treatment time. The power delivered to the airway at the initial power for each group, using the formula above, was calculated as:

$$P_{Airway\ R.6} = 20W * 0.6 = 12W$$

$$P_{Airway\ R.4} = 20W * 0.4 = 8W.$$

Figure 7A:
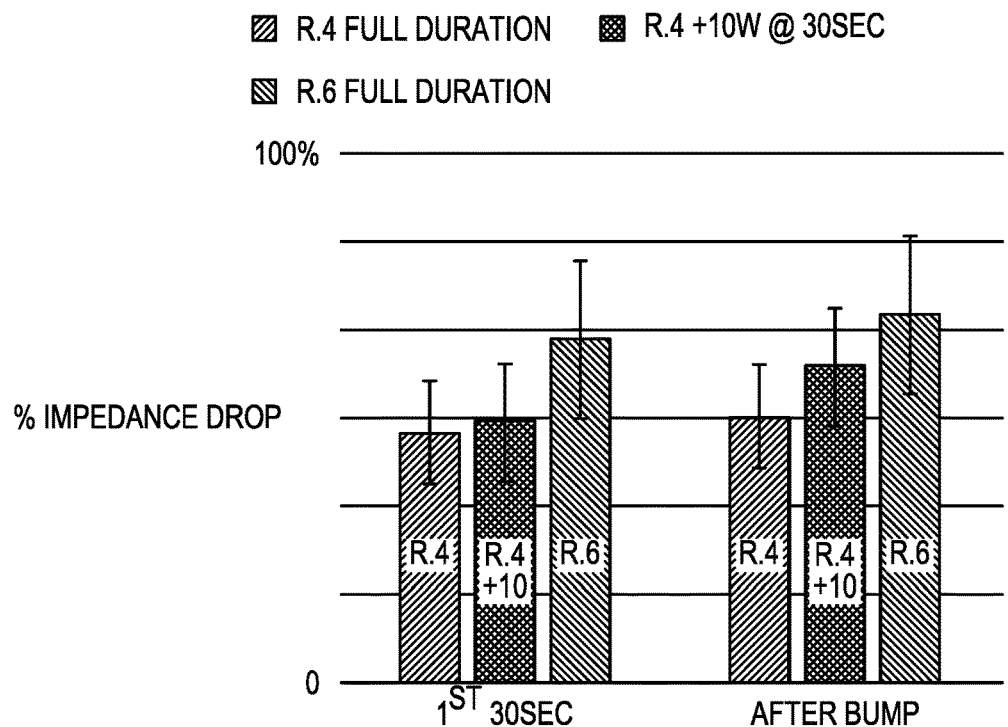
FIGS. 7A and 7B are graphs depicting a general relationship between average current and % impedance drop of the test groups of FIGS. 6A-6C over the course of a treatment.
Figure 7B:
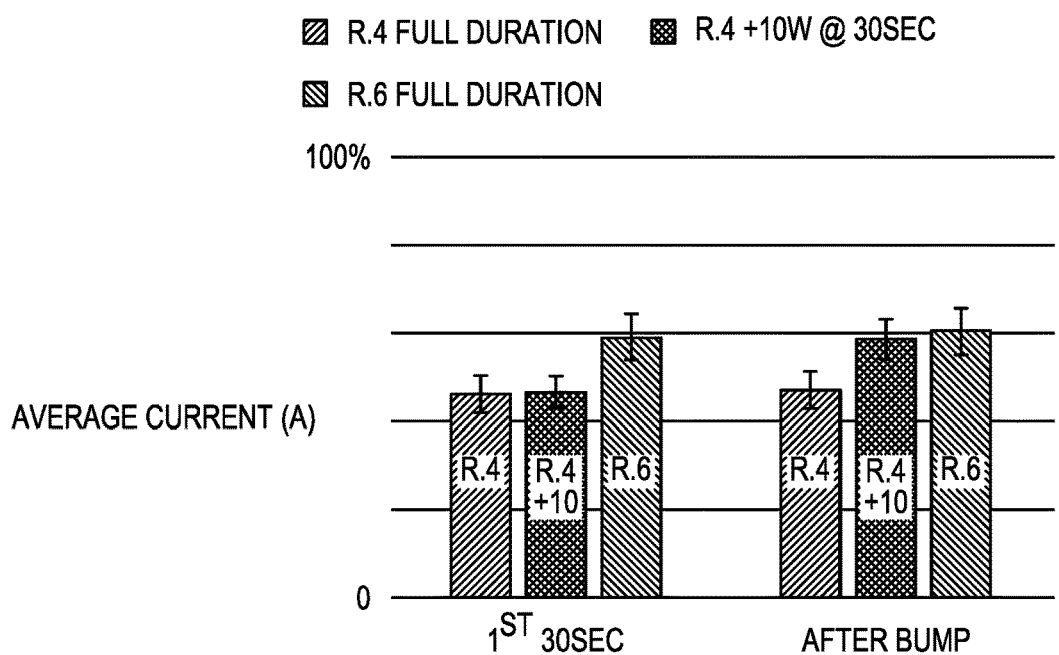

The graphs of FIGS. 7A and 7B indicate that the power bump drives the parameters to match the small bulk resistance group. Specifically, there was a comparable % impedance drop following the power bump because the power bump increases tissue temperature which drives impedance drop. There was also comparable current following the bump because the near field resistance is similar to the small bulk resistance group, which drives similar ablation depth and tissue temperatures.

Change in Target Tissue Temperature as a Function of Impedance

Figure 8:
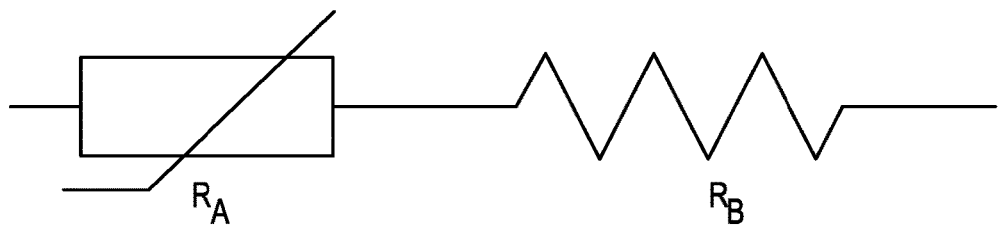
FIG. 8 is a model of a thermistor in series with a resistor to model the airway according to an embodiment of the invention.

As shown in FIG. 8, the airway to be treated can be modeled as a thermistor which is a linear device whose resistance varies with temperature, typically demonstrating a smaller resistance as temperature rises. The body (the resistors in series such as thorax, abdomen, and leg) can be modeled as a fixed resistor, an electrical device whose resistance does not change as a function of temperature. This model is used based on assumptions from the literature demonstrating changes in tissue conductance as a function of temperature. Therefore, the total resistance of the system includes $R_A$, the resistance of the airway represented by a thermistor, and $R_B$, the total resistance of the body/bulk.

Using this model, the resistance of the airway, $R_A$, can be represented as a thermistor with the governing equation of:

$$\frac{1}{RA} = kT_A,$$

where k is a constant representing the linear relationship between conductance of the thermistor, and $T_A$ is the temperature of the airway thermistor. Rewriting this equation to solve for airway to solve for airway temperature is as follows:

$$TA = \frac{1}{kRA}$$

Thus, to find a measurable correlation of the change in temperature in the airway as a function of resistance:

$$TA = TA1 - TA0 = \frac{1}{k}\left(\frac{1}{RA1} - \frac{1}{RA0}\right)$$

Since $R_{A1}$ and $R_{A0}$ cannot be directly measured, the following can be determined:

$$R_T = R_A R_B,$$

and $$R_{A1} = R_{T1} - R_{B1}$$

$$R_{A0} = R_{T0} - R_{B0}.$$

Therefore, from the above equation, $$\left(\frac{1}{RA1} - \frac{1}{RA0}\right) = \left(\frac{1}{RT1-RB1} - \frac{1}{RT0-RB0}\right).$$

Then, multiplying everything on the right side of the equation by 1 yields:

$$\Delta T_A = T_{A1} - T_{A0} =$$

$$\frac{1}{k}\left(\left(\frac{RT0-RB0}{RT0-RB0}\right) \cdot \left(\frac{1}{RT1-RB1}\right) - \left(\frac{RT1-RB1}{RT1-RB1}\right) \cdot \left(\frac{1}{RT0-RB0}\right)\right)$$

Now, recalling that for purposes of the modeling, the resistance of the body does not change such that:

$$R_B = R_{B1} = R_{B0},$$

So that the above equation can be simplified as:

$$\Delta T_A =$$

$$T_{A1} - T_{A0} = \frac{1}{k}\left(\left(\frac{RT0-RB}{RT0-RB}\right) \cdot \left(\frac{1}{RT1-RB}\right) - \left(\frac{RT1-RB}{RT1-RB}\right) \cdot \left(\frac{1}{RT0-RB}\right)\right)$$

Collecting terms yields:

$$\Delta T_A = T_{A1} - T_{A0} = \frac{1}{k}\left(\frac{RT0-RT1}{(RT0-RB) \cdot (RT1-RB)}\right).$$

Pulling the negative sign outside of the equation on the right yields:

$$\Delta T_A = T_{A1} - T_{A0} = -\frac{1}{k}\left(\frac{RT1-RT0}{(RT0-RB) \cdot (RT1-RB)}\right),$$

which is the same as:

$$\Delta T_A = T_{A1} - T_{A0} = -\frac{1}{k}\left(\frac{RT1-RT0}{RA1 \cdot RA0}\right).$$

Therefore, in this model, change in tissue temperature over time of the airway wall ($\Delta T_A$) during non-steady state conditions is proportional to the impedance drop ($R_{T1} - R_{T0}$) divided by the product of the airway wall resistances ($R_{A1} \cdot R_{A0}$) over time.

Figure 9:
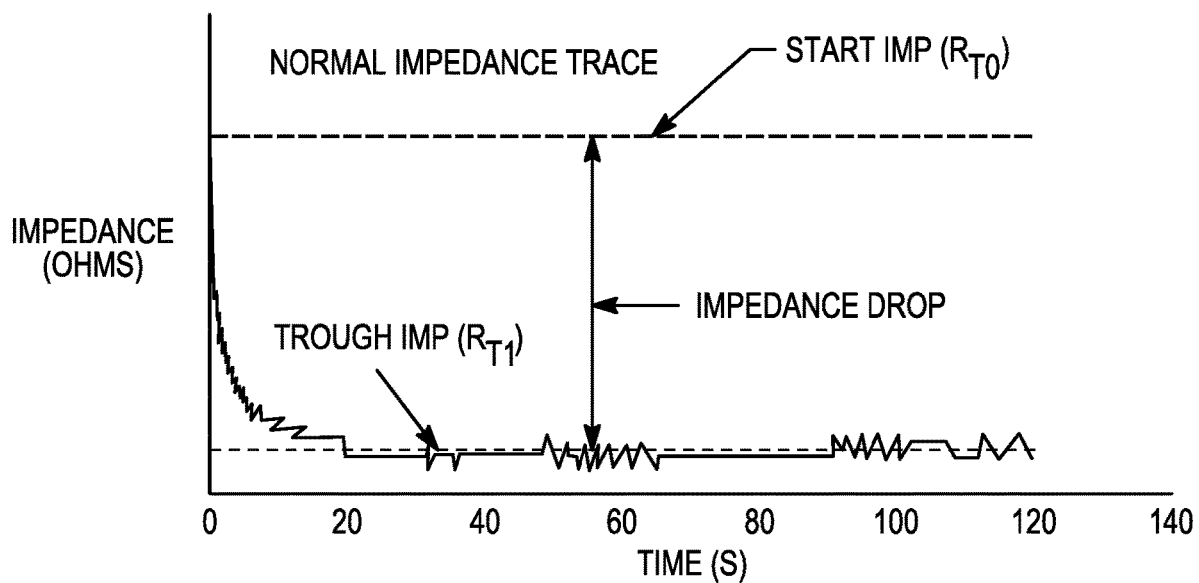
FIG. 9 is an impedance trace during an ablation treatment according to an embodiment of the invention.

% Impedance Drop, Ratio of Change in Impedance to Product of Start and Trough Impedance Now referring to FIG. 9, impedance over time of the treatment can be measured between the active electrode and dispersive electrode. A typical impedance trace shows that as the time begins, an initial impedance ($R_{T0}$) is measured. Impedance drops off rapidly within the first 20-30 seconds of treatment as the tissue heats to reach a trough impedance ($R_{T1}$), in which no further significant decrease in impedance is observed. As discussed above, the impedance drop is the difference between the initial impedance ($R_{T0}$) and the trough impedance ($R_{T1}$). Therefore, the percent (%) impedance drop can also be calculated as follows:

$$\% \text{ Impedance Drop} = \frac{RT0 - RT1}{RT0}$$

Percent impedance drop occurs only in near field tissue due to tissue heating, dissociation of ions, and excitation of ions. This may provide real time feedback on ablation and could provide insight into the impedance inherent to the airway wall.

Additional or alternatively, with this information, the ratio of a change in impedance to the product of the start and trough impedance can also provide real time feedback on ablation and could provide insight into the impedance inherent to the airway wall. The ratio can be calculated as follows:

$$\Delta \text{Ratio} = \frac{RT0 - RT1}{RT0 \cdot RT1}$$

Figure 10A:
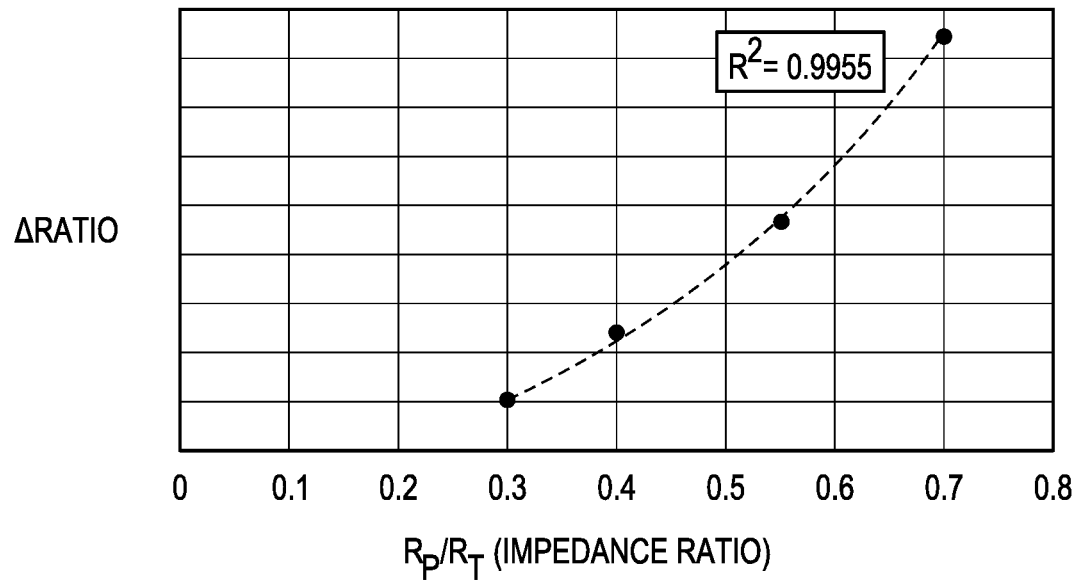
FIGS. 10A-10C are linear regression curves for correlating an impedance ratio with percent impedance drop, change in impedance ratio, and current.
Figure 10B:
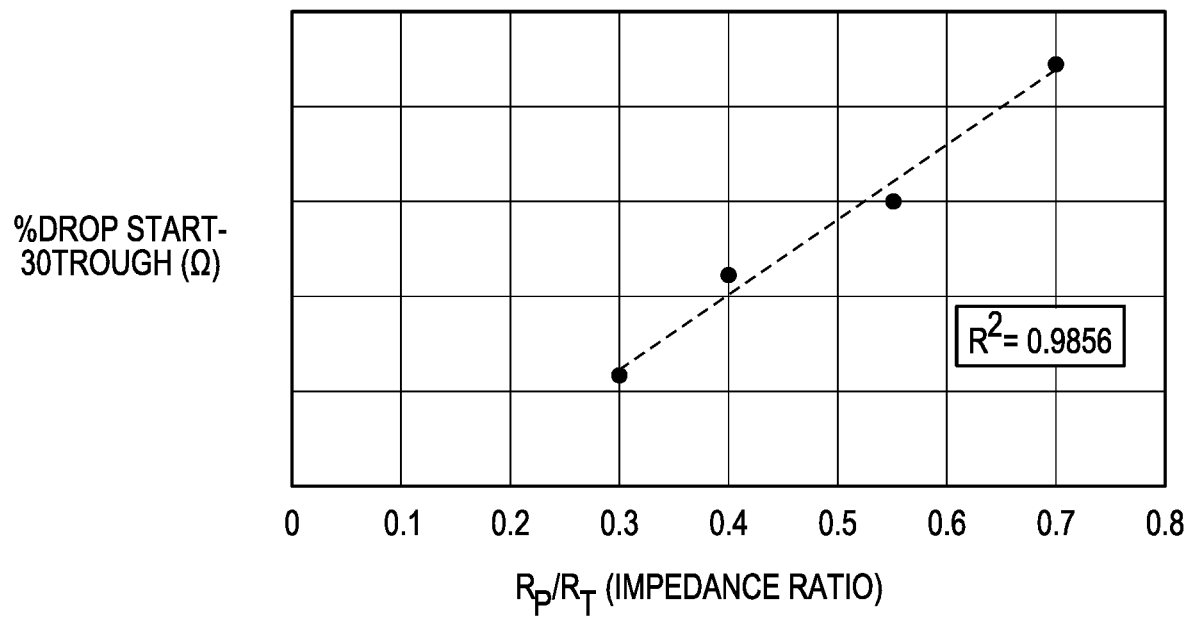
Figure 10C:
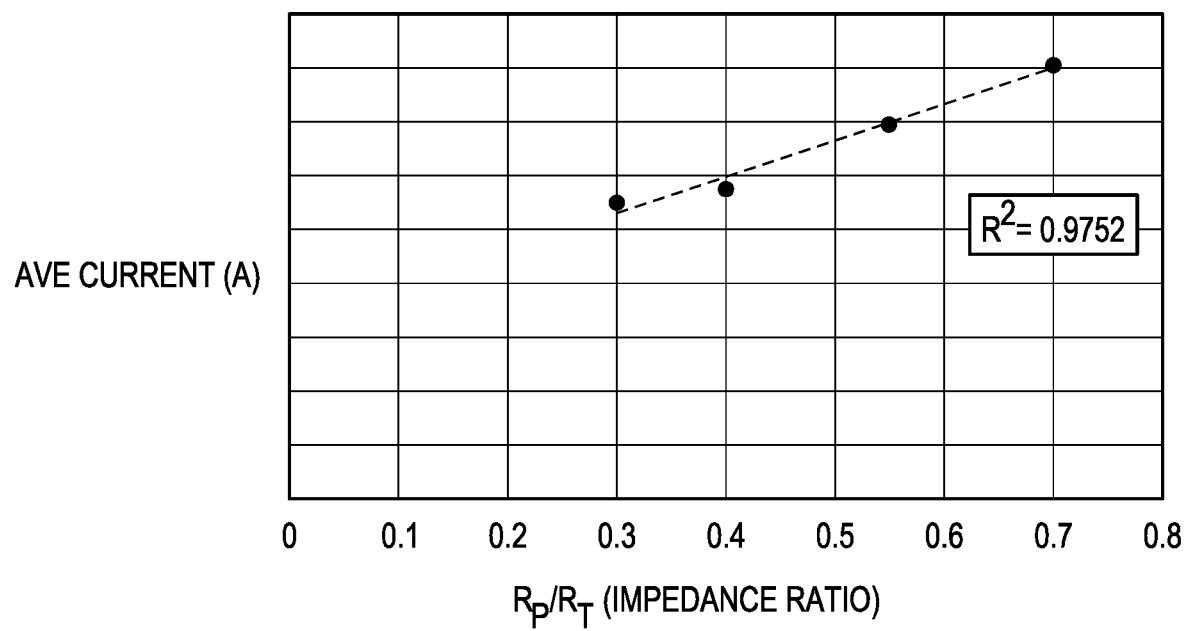

Referring now to FIGS. 10A-10C, bench top ablation using a meat product (i.e., pork chop) to simulate the tissue of the airway wall was used to confirm whether % impedance drop, ΔRatio, and the current are proportional to an impedance ratio. Different impedance ratios ($R_{AW}/R_{Tot}$) of 0.3, 0.4, 0.55, and 0.7 were evaluated at a constant power setting of 32 W. As shown, each of % impedance drop, ΔRatio, and the current were proportional to the impedance ratio, with high R-squared values of over 95%.

Figure 11A:
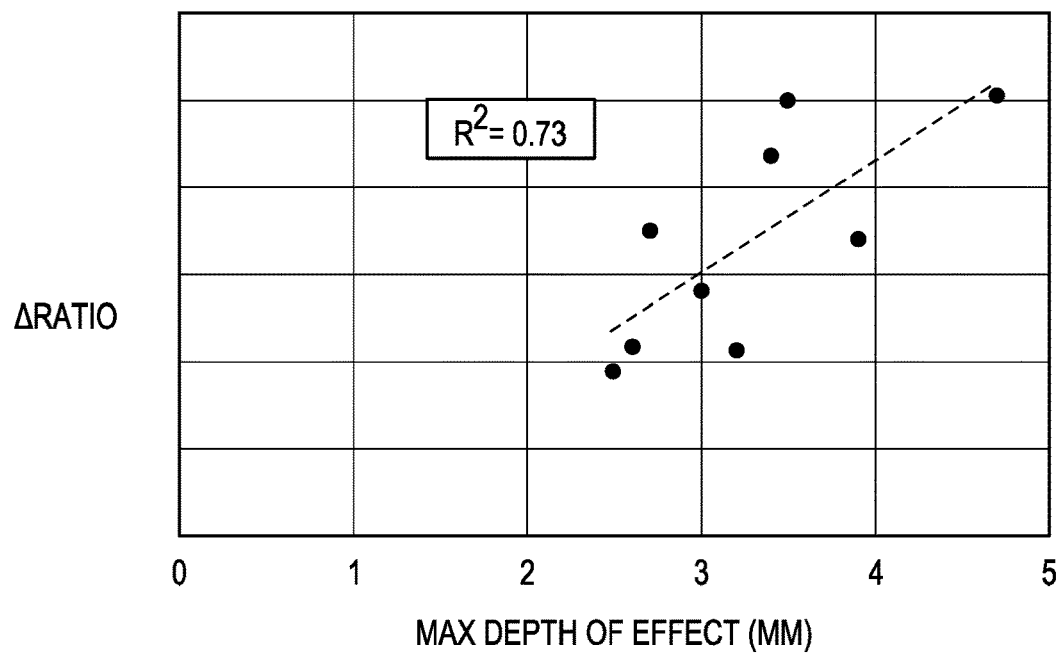
FIGS. 11A-C are plots of maximum lesion depth as a function of percent impedance drop, change in impedance ratio, and current.
Figure 11B:
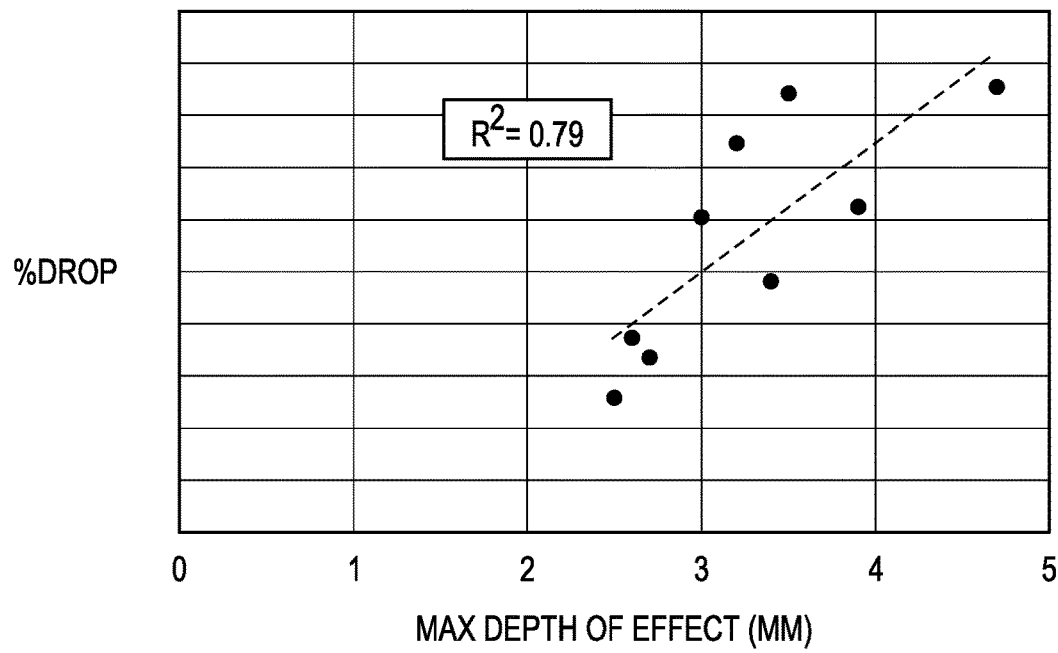
Figure 11C:
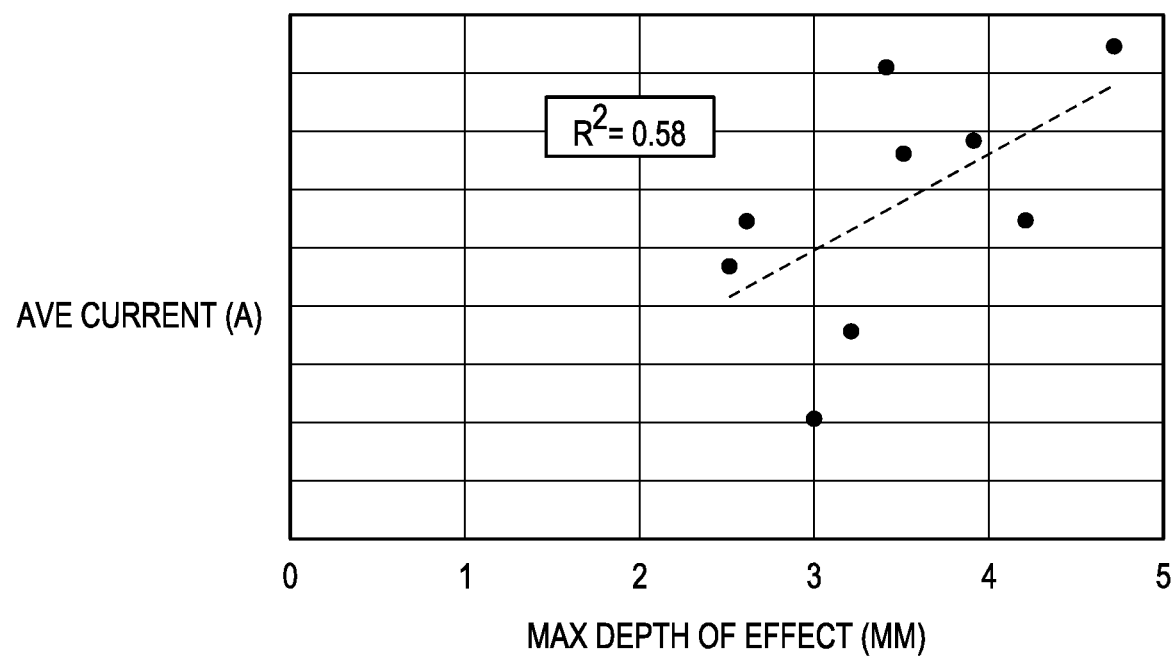

Now referring to FIGS. 11A-11C, the correlation between depth of effect (i.e., ablation lesion) and each of % impedance drop, ΔRatio, and current was studied using animal models. As shown, as each of % impedance drop, ΔRatio, and current increases, the depth of effect increases, with acceptable R-squared values of over 50%.

Based on the theories and models above, various algorithms can be contemplated for compensating for the variability in patient tissue, and therefore resistance, in real time, i.e., during treatment, to achieve improved treatment efficacy.

Treatment Algorithms

Figure 12:
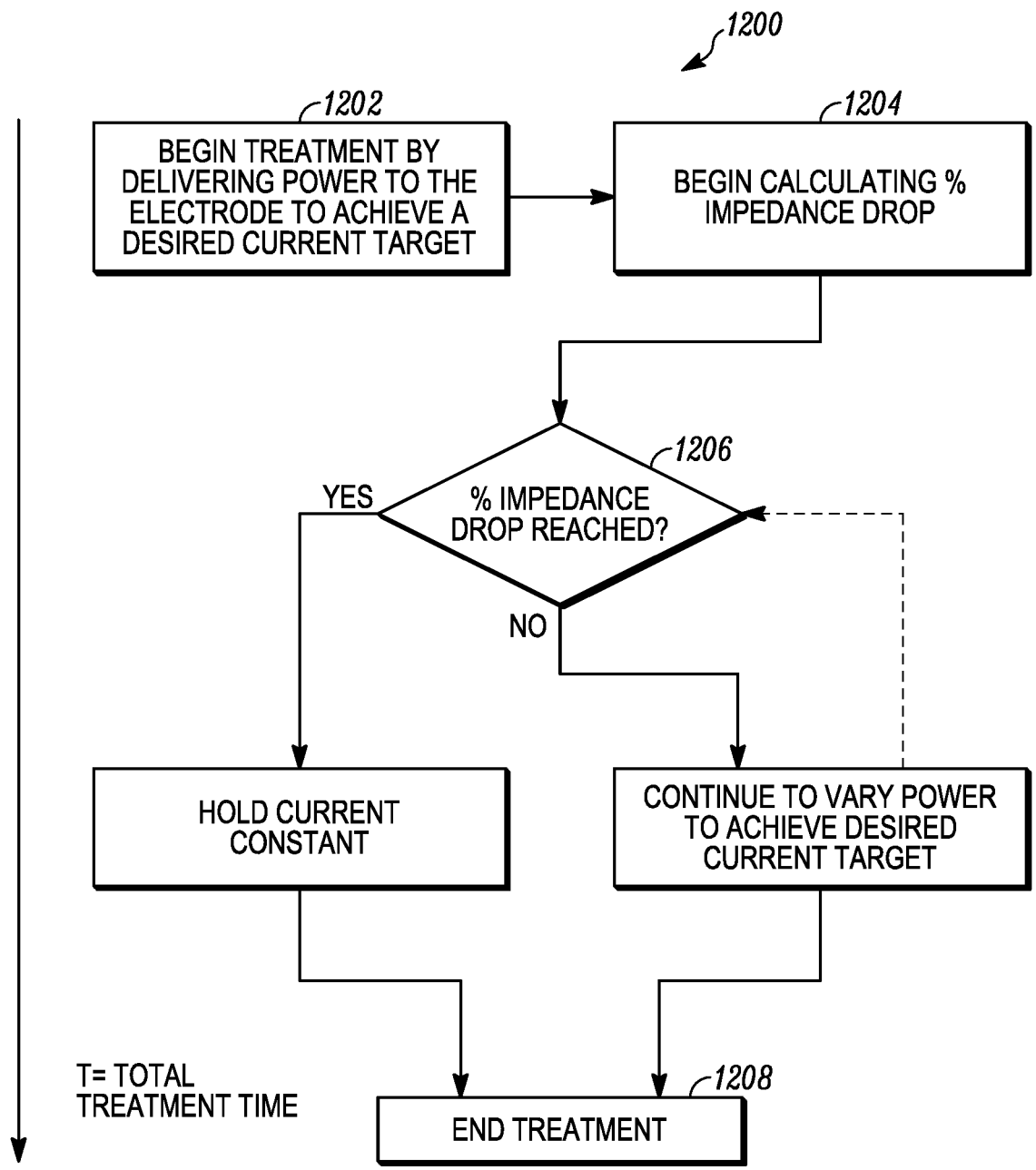
FIG. 12 is a process flow diagram for a treatment method according to an embodiment of the invention.

Using the mathematical models above, in a first embodiment, and referring to FIG. 12, a method of treatment 1200 includes beginning a treatment 1202 at time=0 by delivering a current to the electrode via the generator of the console. A desired current target is set by a user or programmed into the console. In a non-limiting embodiment, the desired current target can be in a range of about 0.1 Amp (A) to about 1.0 A, and more specifically, for a high current target, from about 0.3 A to about 0.7 A, with a preferred default of 0.5 A, and for a low current target, from about 0.2 A to about 0.5 A, with a preferred default of 0.4 A, in increments of 0.05 A. In this embodiment, the power to the electrode is varied to maintain the desired current target, and must operate within a maximum power of the generator (e.g., 50 W) or the generator will automatically shut off.

In this embodiment, at 1204, the console is programmed to begin calculating a impedance drop of:

$$\% \text{ Impedance Drop} = \frac{RT0 - RTactual}{RT0}$$

and will continue calculating the % impedance drop during the entirety of the treatment length. A target % impedance drop is also programmed into the console. In a non-limiting embodiment, the target % impedance drop can be in a range of from about 5% to about 40%, for both low and high drop targets, with a preferred target of 32%.

At 1206, at anytime during the treatment, if the % impedance drop target is reached before the current target, then the console is programmed to maintain the current as measured at the % drop target for the remaining treatment time. If the % impedance drop target is not reached, then the console is programmed to maintain the current target for the rest of the treatment time. In a non-limiting embodiment, the treatment time can be approximately two minutes. At 1208, at the end of the treatment time, the console stops the generator from delivering current to the electrode.

In another embodiment (not shown), a constant current is delivered to the electrode for the entire treatment time within the limits of the maximum power of the generator of the system. In this embodiment, the power is adjusted (within the maximum power limit) to maintain the desired constant current target. Similar to the previous embodiment, the desired current target can be in a range of about 0.1 Amp (A) to about 1.0 A, and more specifically, for a high current target, from about 0.3 A to about 0.7 A, with a preferred default of 0.5 A, and for a low current target, from about 0.2 A to about 0.5 A, with a preferred default of 0.4 A, in increments of 0.05 A. In this embodiment, the power of the generator is varied to maintain the desired current target, and must operate within a maximum power of the generator (e.g., 50 W) or the generator will automatically shut off. Impedance response is not used as a parameter in this embodiment.

In yet another embodiment (not shown), the console adjusts the current (within the maximum power setting of the generator) to maintain a desired % impedance drop, calculated continually from time=0 during the entirety of the treatment. Similar to the previous embodiment of FIG. 9, the target % impedance drop can be in a range of from about 5% to about 40%, for both low and high drop targets, with a preferred target of 32%.

Figure 13:
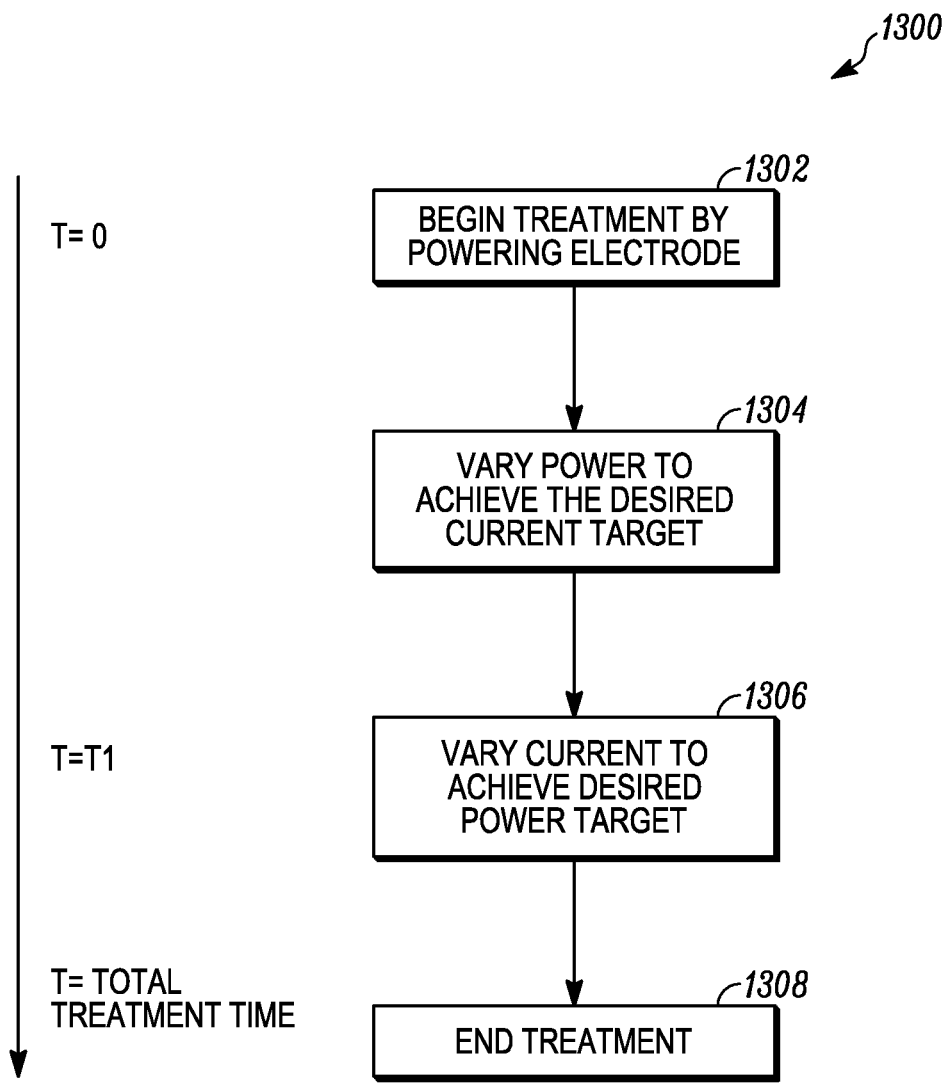
FIG. 13 is a process flow diagram for a treatment method according to another embodiment of the invention.

In yet another embodiment, and referring to FIG. 13, a method of treatment 1300 includes beginning a treatment 1302 at time=0 by delivering a current to the electrode via the generator of the console. A desired current target is set by a user or programmed into the console. In a non-limiting embodiment, the desired current target can be in a range of about 0.1 Amp (A) to about 1.0 A, and more specifically, for a high current target, from about 0.3 A to about 0.7 A, with a preferred default of 0.5 A, and for a low current target, from about 0.2 A to about 0.5 A, with a preferred default of 0.4 A, in increments of 0.05 A. In this embodiment, the power of the generator is dynamically varied to maintain the desired current target, and must operate within a maximum power of the generator (e.g., 50 W) or the generator will automatically shut off.

At 1304, the desired current target is delivered for a first time interval of a total treatment time, for example, for the first 30 seconds of a two minute treatment time. During the first time interval, impedance values are monitored, and a sample of the lower impedance value ($Z_{30}$) during that time interval is monitored. At 1306, upon expiration of the first time interval, the system switches from constant current to constant power, within the selected maximum power limit. In a non-limiting embodiment, the power limit is in a range of about 30 W to about 50 W, with a preferred defaults of 40 W for high power settings and 34 W for low treatment settings.

During this second interval of treatment time, the power is held constant until the total treatment time has expired and impedance continues to be measured and monitored. If, however, the measured impedance is greater than the sum of the lowest impedance value of the first time interval and a predetermined impedance value ($Z_{30}+Z_{D2}$), the console will proceed to a warning mode, or will shut down entirely. In a non-limiting embodiment, the predetermined impedance value ($Z_{D2}$) is about 25 ohms. If no such occurrence during treatment, at 1308, upon expiration of the treatment time, the console stops delivering current to the electrode.

Figure 14:
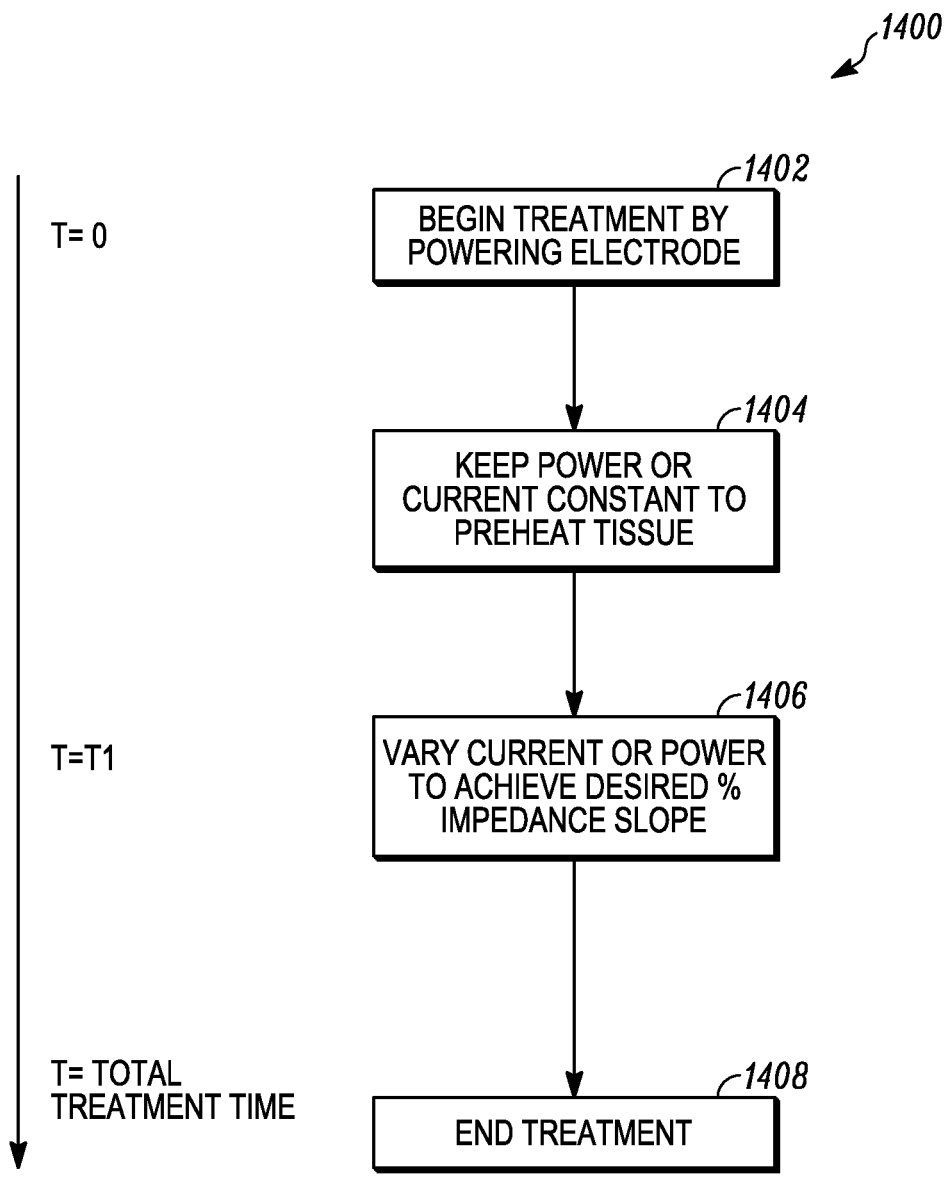
FIG. 14 is a process flow diagram for a treatment method according to yet another embodiment of the invention.

In yet another embodiment of the invention and referring to FIG. 14, to further improve the normalization or maximization of near field tissue heating, a method 1400 includes adjusting power of the system to maintain a small, positive impedance slope during an ablation or treatment. This small positive slope in impedance correlates with a slow rise in impedance, which may result in a more effective or durable treatment because charring or overheating of tissue is avoided. A positive slope represents a skewing of the heating/cooling balance in a direction of more heating, without over-heating the tissue. Over-heating/charring of tissue would be exhibited by a fast rise in impedance or large positive impedance slope. With this method, all ablations or treatments are brought to similar maximum tissue temperatures, regardless of near field tissue impedance variability or variability in electrode contact.

Specifically, at 1402, the treatment begins by powering the electrode. At 1404, for a first time interval, such as but not limited to 30 seconds, a target power or a target current is delivered to the electrode to pre-heat the tissue to be treated. Impedance is measured and monitored continuously at this time, and a percent impedance slope is calculated by the following:

$$\% \text{ Impedance Slope} = \left(\frac{Z0 - Zactual}{t0 - tactual}\right) \cdot 100\%$$

Optionally, during the first time interval, an impedance limit threshold, such as, for example, 10 ohms above the starting impedance, can be set to prevent any run away impedance conditions.

At 1406, after expiration of the first time interval, for the remaining treatment time or a second time interval, such as but not limited to 90 seconds, power and/or current are dynamically varied (within maximum limits) to maintain a target impedance slope. In a non-limiting example, the target impedance slope is in a range from about 1% to about 30%, within maximum power and/or current limits in a range of about 26 W-38 W and 0.3 A-0.5 A, respectively. Optionally, during the second time interval, an impedance limit threshold, such as, for example, 10-50 ohms above the lowest impedance value of the first time interval, or a maximum percent slope value, such as 10%-90% (depending on the target impedance slope) can be set to prevent any run away impedance conditions. If the maximum impedance, current, and/or power limits are reached, the console will proceed to a warning mode, or will shut down entirely. If no such occurrence, then at 1408, at the end of the treatment time, the console stops delivering current to the electrode. The treatment time can be either a set time, e.g. two minutes total, or it can vary based on the % impedance slope to achieve the desired effect.

Figure 15:
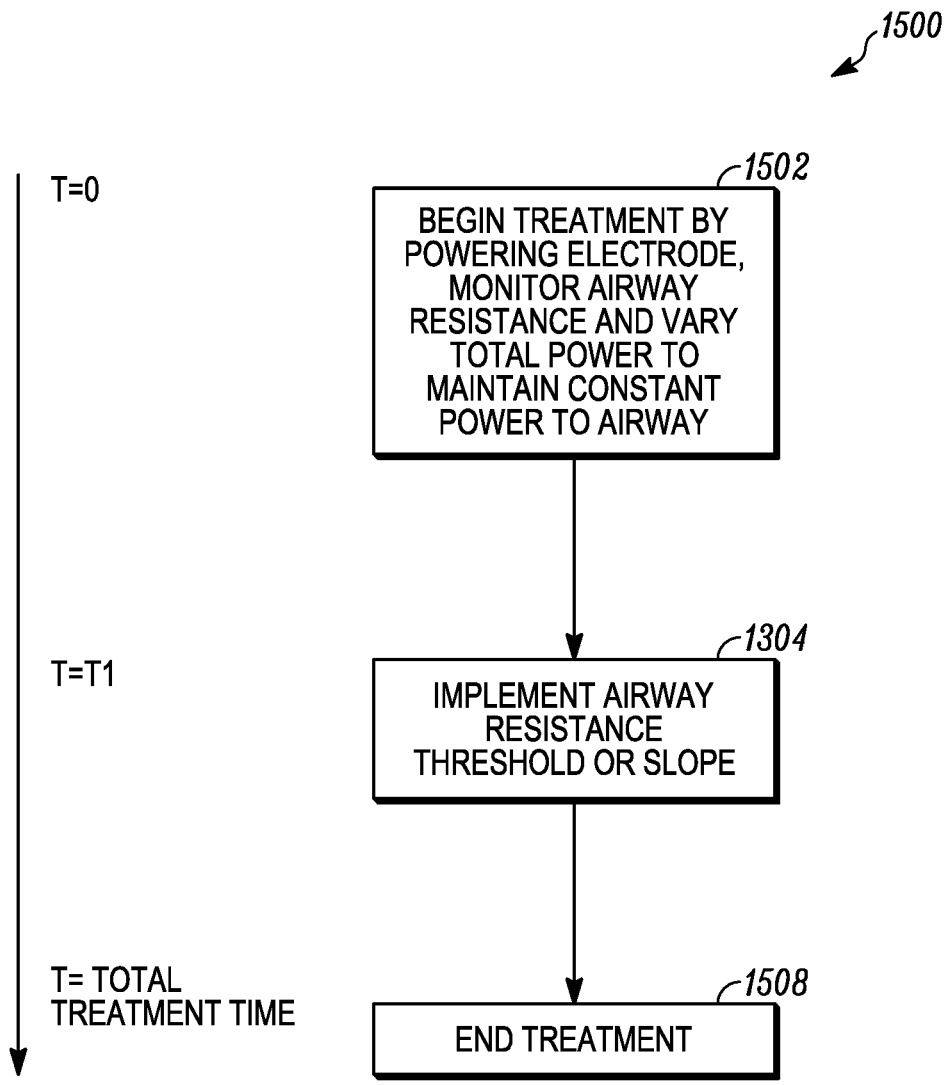
FIG. 15 is a process flow diagram for a treatment method according to yet another embodiment of the invention.

In yet another embodiment of the invention and referring to FIG. 15, to further improve the consistency of the ablation produced in the airway, a method that utilizes an additional electrode of set of electrodes to determine or closely approximate the tissue resistance of the airway $R_A$ during active treatment to maintain a constant power delivery to the airway wall $P_A$ despite variation in bulk resistance. In a monopolar RF system the power delivered to the target tissue for therapeutic effect various significantly from patient to patient based on the variability of the electrical properties and amount of tissue that forms the patient resistive component $R_T$ of the monopolar circuit, FIG. 4. Thus, two patients with the same airway wall resistance, different total resistance $R_T$ treated at the same total power will have different amounts of power deposited in the airway wall. It is known that using normal monopolar systems that only monitor total patient resistance $R_T$, the amount of power delivered to the airway wall will vary proportionally based on the ratio of airway resistance to total resistance.

$$P_A = (R_A/(R_T)) \times P_T$$

With this method, all ablations or treatments are conducted with the same power being deposited in the airway wall, regardless of near field tissue impedance variability, or bulk tissue impedance variability.

Specifically, using this method at 1502 $R_A$ is actively monitored continuously during activation. The total power $P_T$ is then varied in response to changes in $R_A$ to maintain a constant power deposited in the airway wall $P_A$. In a non-limiting example, the target power ranges for $P_A$ could vary between 11 W and 23 W. Optionally, at 1504 a impedance threshold for $R_A$ could be set, such as, for example, 10-50 ohms above the lowest impedance value of the first 30 seconds of energy delivery, or a maximum percent slope value, such as 10%-90% (depending on the target impedance slope) can be set to prevent any run away impedance conditions.

By incorporation of one or more of the algorithms, treatment variability, such as variability in patient tissue and/or electrode contact, can be reduced, thereby enhancing the efficacy and durability of the ablation treatment.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A system for ablating target tissue of an airway of a patient during a treatment, the system comprising:
    an ablation assembly, the ablation assembly being configured to be positioned within the airway, the ablation assembly including an active energy emitter configured to contact an airway wall of the airway, and wherein the active energy emitter is configured to deliver energy to the target tissue of the airway to ablate the target tissue, the target tissue being spaced radially outward from the energy emitter; and
    a controller configured to control energy delivery from an energy source to the energy emitter, wherein the controller is configured to modify one of power and current of the system to achieve a predetermined output value during at least a portion of a treatment time,
    wherein the predetermined output value is a current target, wherein an impedance of tissue at an energy emitter tissue interface is measured during the treatment time, and wherein the controller is configured to:
        hold the current constant if a predetermined impedance target is reached before the current target is reached; or
        vary the power to achieve the current target if the predetermined impedance target is not met during the treatment time,
    wherein the predetermined impedance target is a percent impedance drop calculated by:

$$\% \text{ Impedance Drop} = \frac{RT0 - RTactual}{RT0} \cdot 100\%,$$

in which $R_{T0}$ is an impedance at a beginning of the treatment time, and $R_{Tactual}$ is an impedance at a time t during the treatment time.

2. The system of claim 1, wherein the power is dynamically varied during at least a portion of the treatment time to achieve the current target.

3. The system of claim 2, wherein the power is varied within a maximum power level.

4. The system of claim 1, wherein the controller is configured to dynamically vary the power of the energy source to achieve the current target for a first portion of the treatment time, and upon expiration of the treatment time, the controller is configured to dynamically vary the current of the energy source to achieve a power target for a second portion of the treatment time.

5. The system of claim 4, wherein a sample of a lowest impedance value during the first portion of the treatment time is measured, and wherein the system is configured to indicate a warning or stop delivering energy if an impedance measured during the second portion of the treatment time exceeds a sum of the lower impedance value from the first portion of time and a predetermined impedance value.

6. The system of claim 1, wherein the controller is configured to hold one of power or current constant for a first portion of the treatment time,
   wherein during a second portion of the treatment time, the controller is configured to calculate a percent impedance slope by:

$$\% \text{ Impedance Slope} = \left(\frac{Z0 - Zactual}{t0 - tactual}\right) \cdot 100\%,$$

in which $Z_O$ is an impedance at a beginning of the treatment time, and $Z_{actual}$ is an impedance at a time t during the treatment time, and $t_0-t_{actual}$ is the time elapsed from the beginning of the treatment time, and
   wherein the controller is configured to vary the power or current to maintain the % impedance slope within a predetermined range.

7. The system of claim 6, wherein impedance is measured during the first portion of the treatment time, and wherein the system is configured to indicate a warning or stop delivering energy if a predetermined impedance threshold is met or exceeded during the first portion of the treatment time.

8. The system of claim 7, wherein a sample of a lowest impedance value during the first portion of the treatment time is measured, and wherein the system is configured to indicate a warning or stop delivering energy if an impedance measured during the second portion of the treatment time exceeds a sum of the lower impedance value from the first portion of time and a predetermined impedance value.

9. The system of claim 6, wherein the system is configured to indicate a warning or stop delivering energy if a predetermined % impedance slope value is met or exceeded during the second portion of the treatment time.

10. A method for ablating target tissue of an airway of a patient, the method comprising:
   providing a catheter assembly including an ablation assembly coupled to the distal end of the elongate shaft, the ablation assembly being configured to be positioned within the airway to deliver energy to the target tissue, the ablation assembly including an energy emitter;
   positioning the ablation assembly within the airway such that the energy emitter is in contact with surface tissue of an airway wall of the airway;
   causing the energy emitter to deliver energy to the airway wall for a treatment time to ablate the target tissue; and
   during energy delivery, varying current to the energy emitter to achieve a predetermined output value during at least a portion of the treatment time, wherein the predetermined output value is a current target, the method further comprising:
   measuring an impedance of tissue in contact with the energy emitter during the treatment time;
   holding the current constant if a predetermined impedance target is reached before the current target is reached; and
   varying the power to achieve the current target if the predetermined impedance target is not met during the treatment time wherein the predetermined impedance target is a percent impedance drop calculated by:

$$\% \text{ Impedance Drop} = \frac{RT0 - RTactual}{RT0} \cdot 100\%,$$

in which $R_{TO}$ is an impedance at a beginning of the treatment time, and $R_{Tactual}$ is an impedance at a time t during the treatment time.

11. The method of claim 10, wherein the power to the energy emitter is varied during at least a portion of the treatment time to achieve the current target.

12. The method of claim 11, wherein the power is varied within a maximum power level.

13. The method of claim 10, the method further comprising varying power to the energy emitter, wherein varying the power includes:
   varying the power to achieve the current target for a first portion of the treatment time; and
   upon expiration of the treatment time, varying the current to achieve a power target for a second portion of the treatment time.

14. The method of claim 13, further comprising:
   measuring a lowest impedance value during the first portion of the treatment time;
   measuring the impedance during the second treatment time; and
   indicating a warning or stopping energy delivery if an impedance measured during the second portion of the treatment time exceeds a sum of the lower impedance value from the first portion of time and a predetermined impedance value.

15. The method of claim 10, the method further comprising:
   holding one of power or current constant at a predetermined level for a first portion of the treatment time;
   during a second portion of the treatment time, measuring impedance and calculating a percent impedance slope by:

$$\% \text{ Impedance Slope} = \left(\frac{Z0 - Zactual}{t0 - tactual}\right) \cdot 100\%,$$

in which $Z_O$ is an impedance at a beginning of the treatment time, and $Z_{actual}$ is an impedance at a time t during the treatment time, and $t_0$–tactual is the time elapsed from the beginning of the treatment time; and
   varying the power or current to maintain the % impedance slope within a predetermined range during the second portion of the treatment time.

16. The method of claim 15, wherein impedance is measured during the first portion of the treatment time, and the method further comprises:
   indicating a warning or stopping energy delivery if a predetermined impedance threshold is met or exceeded during the first portion of the treatment time.

17. The method of claim 16, the method further comprising:
   measuring a lowest impedance value during the first portion of the treatment time, and
   indicating a warning or stopping energy delivery if an impedance measured during the second portion of the treatment time exceeds a sum of the lower impedance value from the first portion of time and a predetermined impedance value.

18. The method of claim 16, further comprising:

indicating a warning or stopping energy delivery if a predetermined % impedance slope value is met or exceeded during the second portion of the treatment time.

\* \* \* \* \*